US009090706B2

(12) United States Patent
Upton et al.

(10) Patent No.: US 9,090,706 B2
(45) Date of Patent: *Jul. 28, 2015

(54) FIBRONECTIN: GROWTH FACTOR CHIMERAS

(75) Inventors: Zee Upton, Kenmore Hills (AU); Derek Van Lonkhuyzen, Morayfield Queensland (AU)

(73) Assignee: QUEENSLAND UNIVERSITY OF TECHNOLOGY, Brisbane, Queensland (AU)

( * ) Notice: Subject to any disclaimer, the term of this patent is extended or adjusted under 35 U.S.C. 154(b) by 0 days.

This patent is subject to a terminal disclaimer.

(21) Appl. No.: 13/511,776

(22) PCT Filed: Nov. 30, 2010

(86) PCT No.: PCT/AU2010/001613
§ 371 (c)(1),
(2), (4) Date: Aug. 9, 2012

(87) PCT Pub. No.: WO2011/063477
PCT Pub. Date: Jun. 3, 2011

(65) Prior Publication Data
US 2013/0004543 A1 Jan. 3, 2013

(51) Int. Cl.
A61K 38/00 (2006.01)
C07K 14/65 (2006.01)
C07K 14/78 (2006.01)
A61K 38/18 (2006.01)
A61K 38/39 (2006.01)

(52) U.S. Cl.
CPC ............... *C07K 14/65* (2013.01); *A61K 38/18* (2013.01); *A61K 38/1808* (2013.01); *A61K 38/1825* (2013.01); *A61K 38/39* (2013.01); *C07K 14/78* (2013.01); *A61K 38/00* (2013.01); *C07K 2319/00* (2013.01); *C07K 2319/50* (2013.01)

(58) Field of Classification Search
None
See application file for complete search history.

(56) References Cited

U.S. PATENT DOCUMENTS

| 4,366,241 | A | 12/1982 | Tom et al. |
| 4,843,000 | A | 6/1989 | Litman et al. |
| 4,849,338 | A | 7/1989 | Litman et al. |
| 5,019,513 | A | 5/1991 | Kasper et al. |
| 5,422,252 | A | 6/1995 | Walker et al. |
| 5,752,019 | A | 5/1998 | Rigoutsos et al. |
| 5,929,040 | A | 7/1999 | Werther et al. |
| 5,936,064 | A | 8/1999 | Baxter |
| 5,958,764 | A | 9/1999 | Roop et al. |
| 5,962,427 | A | 10/1999 | Goldstein et al. |
| 6,054,122 | A | 4/2000 | MacPhee et al. |
| 6,090,790 | A | 7/2000 | Eriksson |
| 2009/0209730 | A1 | 8/2009 | Asada et al. |

FOREIGN PATENT DOCUMENTS

| AU | WO99/54359 | * 10/1999 | ............. C07K 19/00 |
| EP | 0239400 | 9/1987 | |
| EP | 0795606 | 9/1997 | |
| JP | 03232898 | 10/1991 | |
| WO | 9201813 | 2/1992 | |
| WO | 9418232 | 8/1994 | |
| WO | 9719193 | 5/1997 | |
| WO | 9741526 | 11/1997 | |
| WO | 9911789 | 3/1999 | |
| WO | 9947070 | 9/1999 | |
| WO | 9962536 | 12/1999 | |
| WO | WO 00/55206 | * 9/2000 | ............. C07K 14/78 |

OTHER PUBLICATIONS

Kornblihtt et al., EMBO J. 1985, 4: 1755-1759.*
Johansson, Frontiers in Bioscience, 1997; 2: d126-146.*
Phillips, A., J Pharm Pharmacology 53: 1169-1174, 2001.*
Gui and Murphy, J Clin Endocrinol Metab. 2001; 86: 2104-10.*
Huston et al., Methods in Enzymology, 1991; 203: 46-88.*
Uhlén and Moks, Methods Enzymol. 1990; 185: 129-43.*
Battermann, Radiother Oncol. 2000; 57: 269-72.*
Kawase et al., FEBS, 1992; 798: 126-128.*
Fairbrother et al., Structure 1998; 6: 637-648.*
Sharma et al., The EMBO Journal, 1999; 18: 1468-1479.*
Florent Elefteriou, Jean-Yves Exposito, Robert Garrone and Clare Lethias "Characterizaion of Bovine Tenascin-X" The Journal of Biological Chemistry, vol. 272, No. 36, 1997, pp. 22866-22874.
Donald E. Nies, Timothy J. Hemesath, Ji-Hyon Kim, Jeffrey R. Gulcher and Kari Stefansson, "The Complete cDNA Sequence of Human Hexabrachion (Tenascin), A Multidomain Protein Containing Unique Epidermal Growth Factor Repeats" The Journal of Biological Chemistry, vol. 266, No. 6, 1991, pp. 2818-2823.
Jun-Hyeog Jang, and Chong-Pyoung Chung, "Enignering and Expression of a Recombinant Fusion Protein Possessing Fibroblast Growth Factor-2 and Fibronectin Fragment" Biotechnology Letters, 2004, pp. 1837-1840.
Clark et al., "Fibroblast Migration on Fibronectin Requires Three Distinct Functional Domains", The Society for Investigative Dermatology, Inc., 2003, pp. 695-705.
Obara et al., "The Third Type III Module of Human Fibronectin Mediates Cell Adhesion and Migration", Japanese Biochemical Society, 2010, pp. 327-335.

\* cited by examiner

*Primary Examiner* — Christina Borgeest
(74) *Attorney, Agent, or Firm* — Tarolli, Sundheim, Covell & Tummino LLP

(57) ABSTRACT

Isolated protein complexes are provided comprising growth factors such as IGF-I, IGF-II, EGF, bFGF, or KGF and fibronectin, or at least domains thereof that enable binding to and activation of both a growth factor receptor, and an integrin receptor-binding domain of fibronectin. These protein complexes include synthetic proteins where the growth factor and fibronectin sequences are joined by a linker sequence. Also provided are uses of these protein complexes for stimulating or inducing cell migration and/or proliferation in wound healing, tissue engineering, cosmetic and therapeutic treatments such as skin replacement, skin replenishment and treatment of burns where epithelial cell migration is required. In other embodiments, the invention provides inhibition of cancer cell metastasis, particularly in relation to breast cancer.

11 Claims, 3 Drawing Sheets

A) FN AA sequence

```
   1    mlrgpgpgll llavqclgta vpstgasksk rqaqqmvqpq spvavsqskp gcydngkhyq
  61    inqqwertyl gnalvctcyg gsrgfncesk peaeetcfdk ytgntyrvgd tyerpkdsmi
 121    wdctcigagr grisctianr cheggqsyki gdtwrrphet ggymlecvcl gngkgewtck
 181    piaekcfdha agtsyvvget wekpyqgwmm vdctclgegs gritctsrnr cndqdtrtsy
 241    rigdtwskkd nrgnllqcic tngrgewkc erhtsvqtts sgsgpftdvr aavyqpqphp
 301    qpppyghcvt dsgvvysvgm qwlktqgnkq mlctclgngv scqetavtqt yggnsngepc
 361    vlpftyngrt fyscttegrq dghlwcstts nyeqdqkysf ctdhtvlvqt qggnsngalc
 421    hfpflynnhn ytdctsegrr dnmkwcgttq nydadqkfgf cpmaaheeic ttnegvmyri
 481    gdqwdkqhdm ghmmrctcvg ngrgewtcia ysqlrdqciv dditynyndt fhkrheeghm
 541    lnctcfgqgr grwkcdpvdq cqdsetgtfy qigdswekyv hgvryqcycy grgigewhcq
 601    plqtypsssg pvevfitetp sqpnshpiqw napqpshisk yilrwrpkns vgrwkeatip
 661    ghlnsytikg lkpgvvyegq lisiqqyghq evtrfdfttt ststpvtsnt vtgettpfsp
 721    lvatsesvte itassfvvsw vsasdtvsgf rveyelseeg depqyldlps tatsvnipdl
 781    lpgrkyivnv yqisedgeqs lilstsqtta pdappdptvd qvddtsivvr wsrpqapitg
 841    yrivyspsve gsstelnlpe tansvtlsdl qpgvqyniti yaveenqest pvviqqettg
 901    tprsdtvpsp rdlqfvevtd vkvtimwtpp esavtgyrvd vipvnlpgeh gqrlpisrnt
 961    faevtglspg vtyyfkvfav shgreskplt aqqttkldap tnlqfvnetd stvlvrwtpp
1021    raqitgyrlt vgltrrgqpr qynvgpsvsk yplrnlqpas eytvslvaik gnqespkatg
1081    vfttlqpgss ippynteVte ttivitwtpa prigfklgvr psqggeapre vtsdsgsivv
1141    sgltpgveyv ytiqvlrdgq erdapivnkv vtplspptnl hleanpdtgv ltvswerstt
1201    pditgyritt tptngqqgns leevvhadqs sctfdnlspg leynvsvytv kddkesvpis
1261    dtiipavppp tdlrftnigp dtmrvtwapp psidltnflv ryspvkneed vaelsispsd
1321    navvltnllp gteyvvsvss vyeqhestpl rgrqktglds ptgidfsdit ansftvhwia
1381    pratitgyri rhhpehfsgr predrvphsr nsitltnltp gteyvvsiva lngreespll
1441    igqqstvsdv prdlevvaat ptslliswda pavtvryyri tygetggnsp vqeftvpgsk
1501    statisglkp gvdytitvya vtgrgdspas skpisinyrt eidkpsqmqv tdvqdnsisv
1561    kwlpssspvt gyrvttttpkn gpgptktkta gpdqtemtie glqptveyvv svyaqnpsge
1621    sqplvqtavt nidrpkglaf tdvdvdsiki awespqgqvs ryrvtysspe dgihelfpap
1681    dgeedtaelq glrpgseytv svvalhddme sqpligtqst aipaptdlkf tqvtptslsa
1741    qwtppnvqlt gyrvrvtpke ktgpmkeinl apdsssvvvs glmvatkyev svyalkdtlt
1801    srpaqgvvtt lenvspprra rvtdatetti tiswrtktet itgfqvdavp angqtpiqrt
1861    ikpdvrsyti tglqpgtdyk iylytlndna rsspvvidas taidapsnlr flattpnsll
1921    vswqpprari tgyiikyekp gspprevvpr prpgvteati tglepgteyt iyvialknnq
1981    kseplligrkk tdelpqlvtl phpnlhgpei ldvpstvqkt pfvthpgydt gngiqlpgts
2041    gqqpsvgqqm ifeehgfrrt tppttatpir hrprpyppnv geeiqighip redvdyhlyp
2101    hgpglnpnas tgqealsqtt iswapfqdts eyiischpvg tdeeplqfrv pgtstsatlt
2161    gltrgatyni ivealkdqqr hkvreevvtv gnsvneglnq ptddscfdpy tvshyavgde
2221    wermsesgfk llcqclgfgs ghfrcdssrw chdngvnyki gekwdrqgen gqmmsctclg
2281    ngkgefkcdp heatcyddgk tyhvgeqwqk eylgaicsct cfggqrgwrc dncrrpggep
2341    spegttgqsy nqysqryhqr tntnvncpie cfmpldvqad redsre (SEQ ID NO:1)
```

B) IGF-I AA sequence

GPETLCGAEL VDALQFVCGD RGFYFNKPTG YGSSSRRAPQ TGIVDECCFR SCDLRRLEMY
CAPLKPAKSA (SEQ ID NO:2)

C) IGF-II AA sequence

AYRPSETLCG GELVDTLQFV CGDRGFYFSR PASRVSRRSR GIVEECCFRS CDLALLETYC
ATPAKSE (SEQ ID NO:3)

FIGURE 1

D) EGF AA sequence

NSDSECPLSH DGYCLHDGVC MYIEALDKYA CNCVVGYIGE RCQYRDLKWW ELR (SEQ ID NO:4)

E) bFGF AA sequence

PALPEDGGSG AFPPGHFKDP KRLYCKNGGF FLRIHPDGRV DGVREKSDPH IKLQLQAEER
GVVSIKGVCA NRYLAMKEDG RLLASKCVTD ECFFFERLES NNYNTYRSRK YTSWYVALKR
TGQYKLGSKT GPGQKAILFL PMSAKS (SEQ ID NO:5)

F) KGF AA sequence

CNDMTPEQMA TNVNCSSPER HTRSYDYMEG GDIRVRRLFC RTQWYLRIDK RGKVKGTQEM
KNNYNIMEIR TVAVGIVAIK GVESEFYLAM NKEGKLYAKK ECNEDCNFKE LILENHYNTY
ASAKWTHNGG EMFVALNQKG IPVRGKKTKK EQKTAHFLPM AIT (SEQ ID NO:6)

G) Linker Sequences

1) $Gly_4$ Ser (SEQ ID NO:7)
2) $Gly_4$ $Ser_3$ (SEQ ID NO:8)
3) $(Gly_4\ Ser)_3$ (SEQ ID NO:9)
4) $(Gly_4\ Ser)_4$ (SEQ ID NO:10)
5) Leu Ile Lys Met Lys Pro (SEQ ID NO:11)
6) Gln Pro Gln Gly Leu Ala Lys (SEQ ID NO:12)

FIGURE 1 cont'd

SEQUENCE LISTING

<160> NUMBER OF SEQ ID NOS: 12

<210> SEQ ID NO 1
<211> LENGTH: 2386
<212> TYPE: PRT
<213> ORGANISM: Homo sapiens

<400> SEQUENCE: 1

Met Leu Arg Gly Pro Gly Pro Gly Leu Leu Leu Leu Ala Val Gln Cys
1               5                   10                  15

Leu Gly Thr Ala Val Pro Ser Thr Gly Ala Ser Lys Ser Lys Arg Gln
            20                  25                  30

Ala Gln Gln Met Val Gln Pro Gln Ser Pro Val Ala Val Ser Gln Ser
        35                  40                  45

Lys Pro Gly Cys Tyr Asp Asn Gly Lys His Tyr Gln Ile Asn Gln Gln
    50                  55                  60

-continued

```
Trp Glu Arg Thr Tyr Leu Gly Asn Ala Leu Val Cys Thr Cys Tyr Gly
 65                  70                  75                  80

Gly Ser Arg Gly Phe Asn Cys Glu Ser Lys Pro Glu Ala Glu Glu Thr
                 85                  90                  95

Cys Phe Asp Lys Tyr Thr Gly Asn Thr Tyr Arg Val Gly Asp Thr Tyr
                100                 105                 110

Glu Arg Pro Lys Asp Ser Met Ile Trp Asp Cys Thr Cys Ile Gly Ala
            115                 120                 125

Gly Arg Gly Arg Ile Ser Cys Thr Ile Ala Asn Arg Cys His Glu Gly
130                 135                 140

Gly Gln Ser Tyr Lys Ile Gly Asp Thr Trp Arg Arg Pro His Glu Thr
145                 150                 155                 160

Gly Gly Tyr Met Leu Glu Cys Val Cys Leu Gly Asn Gly Lys Gly Glu
                165                 170                 175

Trp Thr Cys Lys Pro Ile Ala Glu Lys Cys Phe Asp His Ala Ala Gly
                180                 185                 190

Thr Ser Tyr Val Val Gly Glu Thr Trp Glu Lys Pro Tyr Gln Gly Trp
            195                 200                 205

Met Met Val Asp Cys Thr Cys Leu Gly Glu Gly Ser Gly Arg Ile Thr
210                 215                 220

Cys Thr Ser Arg Asn Arg Cys Asn Asp Gln Asp Thr Arg Thr Ser Tyr
225                 230                 235                 240

Arg Ile Gly Asp Thr Trp Ser Lys Lys Asp Asn Arg Gly Asn Leu Leu
                245                 250                 255

Gln Cys Ile Cys Thr Gly Asn Gly Arg Gly Glu Trp Lys Cys Glu Arg
                260                 265                 270

His Thr Ser Val Gln Thr Thr Ser Ser Gly Ser Gly Pro Phe Thr Asp
            275                 280                 285

Val Arg Ala Ala Val Tyr Gln Pro Gln Pro His Pro Gln Pro Pro Pro
290                 295                 300

Tyr Gly His Cys Val Thr Asp Ser Gly Val Val Tyr Ser Val Gly Met
305                 310                 315                 320

Gln Trp Leu Lys Thr Gln Gly Asn Lys Gln Met Leu Cys Thr Cys Leu
                325                 330                 335

Gly Asn Gly Val Ser Cys Gln Glu Thr Ala Val Thr Gln Thr Tyr Gly
                340                 345                 350

Gly Asn Ser Asn Gly Glu Pro Cys Val Leu Pro Phe Thr Tyr Asn Gly
            355                 360                 365

Arg Thr Phe Tyr Ser Cys Thr Thr Glu Gly Arg Gln Asp Gly His Leu
370                 375                 380

Trp Cys Ser Thr Thr Ser Asn Tyr Glu Gln Asp Gln Lys Tyr Ser Phe
385                 390                 395                 400

Cys Thr Asp His Thr Val Leu Val Gln Thr Gln Gly Gly Asn Ser Asn
                405                 410                 415

Gly Ala Leu Cys His Phe Pro Phe Leu Tyr Asn Asn His Asn Tyr Thr
                420                 425                 430

Asp Cys Thr Ser Glu Gly Arg Arg Asp Asn Met Lys Trp Cys Gly Thr
            435                 440                 445

Thr Gln Asn Tyr Asp Ala Asp Gln Lys Phe Gly Phe Cys Pro Met Ala
450                 455                 460

Ala His Glu Glu Ile Cys Thr Thr Asn Glu Gly Val Met Tyr Arg Ile
465                 470                 475                 480
```

-continued

Gly Asp Gln Trp Asp Lys Gln His Asp Met Gly His Met Met Arg Cys
                485                 490                 495
Thr Cys Val Gly Asn Gly Arg Gly Glu Trp Thr Cys Ile Ala Tyr Ser
            500                 505                 510
Gln Leu Arg Asp Gln Cys Ile Val Asp Asp Ile Thr Tyr Asn Val Asn
        515                 520                 525
Asp Thr Phe His Lys Arg His Glu Glu Gly His Met Leu Asn Cys Thr
    530                 535                 540
Cys Phe Gly Gln Gly Arg Gly Arg Trp Lys Cys Asp Pro Val Asp Gln
545                 550                 555                 560
Cys Gln Asp Ser Glu Thr Gly Thr Phe Tyr Gln Ile Gly Asp Ser Trp
                565                 570                 575
Glu Lys Tyr Val His Gly Val Arg Tyr Gln Cys Tyr Cys Tyr Gly Arg
            580                 585                 590
Gly Ile Gly Glu Trp His Cys Gln Pro Leu Gln Thr Tyr Pro Ser Ser
        595                 600                 605
Ser Gly Pro Val Glu Val Phe Ile Thr Glu Thr Pro Ser Gln Pro Asn
    610                 615                 620
Ser His Pro Ile Gln Trp Asn Ala Pro Gln Pro Ser His Ile Ser Lys
625                 630                 635                 640
Tyr Ile Leu Arg Trp Arg Pro Lys Asn Ser Val Gly Arg Trp Lys Glu
                645                 650                 655
Ala Thr Ile Pro Gly His Leu Asn Ser Tyr Thr Ile Lys Gly Leu Lys
            660                 665                 670
Pro Gly Val Val Tyr Glu Gly Gln Leu Ile Ser Ile Gln Gln Tyr Gly
        675                 680                 685
His Gln Glu Val Thr Arg Phe Asp Phe Thr Thr Thr Ser Thr Ser Thr
    690                 695                 700
Pro Val Thr Ser Asn Thr Val Thr Gly Glu Thr Thr Pro Phe Ser Pro
705                 710                 715                 720
Leu Val Ala Thr Ser Glu Ser Val Thr Glu Ile Thr Ala Ser Ser Phe
                725                 730                 735
Val Val Ser Trp Val Ser Ala Ser Asp Thr Val Ser Gly Phe Arg Val
            740                 745                 750
Glu Tyr Glu Leu Ser Glu Glu Gly Asp Glu Pro Gln Tyr Leu Asp Leu
        755                 760                 765
Pro Ser Thr Ala Thr Ser Val Asn Ile Pro Asp Leu Leu Pro Gly Arg
    770                 775                 780
Lys Tyr Ile Val Asn Val Tyr Gln Ile Ser Glu Asp Gly Glu Gln Ser
785                 790                 795                 800
Leu Ile Leu Ser Thr Ser Gln Thr Thr Ala Pro Asp Ala Pro Pro Asp
                805                 810                 815
Pro Thr Val Asp Gln Val Asp Asp Thr Ser Ile Val Val Arg Trp Ser
            820                 825                 830
Arg Pro Gln Ala Pro Ile Thr Gly Tyr Arg Ile Val Tyr Ser Pro Ser
        835                 840                 845
Val Glu Gly Ser Ser Thr Glu Leu Asn Leu Pro Glu Thr Ala Asn Ser
    850                 855                 860
Val Thr Leu Ser Asp Leu Gln Pro Gly Val Gln Tyr Asn Ile Thr Ile
865                 870                 875                 880
Tyr Ala Val Glu Glu Asn Gln Glu Ser Thr Pro Val Val Ile Gln Gln
                885                 890                 895
Glu Thr Thr Gly Thr Pro Arg Ser Asp Thr Val Pro Ser Pro Arg Asp

-continued

Leu Gln Phe Val Glu Val Thr Asp Val Lys Val Thr Ile Met Trp Thr
            915                 920                 925
Pro Pro Glu Ser Ala Val Thr Gly Tyr Arg Val Asp Val Ile Pro Val
930                 935                 940
Asn Leu Pro Gly Glu His Gly Gln Arg Leu Pro Ile Ser Arg Asn Thr
945                 950                 955                 960
Phe Ala Glu Val Thr Gly Leu Ser Pro Gly Val Thr Tyr Tyr Phe Lys
                965                 970                 975
Val Phe Ala Val Ser His Gly Arg Glu Ser Lys Pro Leu Thr Ala Gln
            980                 985                 990
Gln Thr Thr Lys Leu Asp Ala Pro Thr Asn Leu Gln Phe Val Asn Glu
        995                 1000                1005
Thr Asp Ser Thr Val Leu Val Arg Trp Thr Pro Pro Arg Ala Gln
        1010                1015                1020
Ile Thr Gly Tyr Arg Leu Thr Val Gly Leu Thr Arg Arg Gly Gln
        1025                1030                1035
Pro Arg Gln Tyr Asn Val Gly Pro Ser Val Ser Lys Tyr Pro Leu
        1040                1045                1050
Arg Asn Leu Gln Pro Ala Ser Glu Tyr Thr Val Ser Leu Val Ala
        1055                1060                1065
Ile Lys Gly Asn Gln Glu Ser Pro Lys Ala Thr Gly Val Phe Thr
        1070                1075                1080
Thr Leu Gln Pro Gly Ser Ser Ile Pro Pro Tyr Asn Thr Glu Val
        1085                1090                1095
Thr Glu Thr Thr Ile Val Ile Thr Trp Thr Pro Ala Pro Arg Ile
        1100                1105                1110
Gly Phe Lys Leu Gly Val Arg Pro Ser Gln Gly Gly Glu Ala Pro
        1115                1120                1125
Arg Glu Val Thr Ser Asp Ser Gly Ser Ile Val Val Ser Gly Leu
        1130                1135                1140
Thr Pro Gly Val Glu Tyr Val Tyr Thr Ile Gln Val Leu Arg Asp
        1145                1150                1155
Gly Gln Glu Arg Asp Ala Pro Ile Val Asn Lys Val Val Thr Pro
        1160                1165                1170
Leu Ser Pro Pro Thr Asn Leu His Leu Glu Ala Asn Pro Asp Thr
        1175                1180                1185
Gly Val Leu Thr Val Ser Trp Glu Arg Ser Thr Thr Pro Asp Ile
        1190                1195                1200
Thr Gly Tyr Arg Ile Thr Thr Thr Pro Thr Asn Gly Gln Gln Gly
        1205                1210                1215
Asn Ser Leu Glu Glu Val Val His Ala Asp Gln Ser Ser Cys Thr
        1220                1225                1230
Phe Asp Asn Leu Ser Pro Gly Leu Glu Tyr Asn Val Ser Val Tyr
        1235                1240                1245
Thr Val Lys Asp Asp Lys Glu Ser Val Pro Ile Ser Asp Thr Ile
        1250                1255                1260
Ile Pro Ala Val Pro Pro Thr Asp Leu Arg Phe Thr Asn Ile
        1265                1270                1275
Gly Pro Asp Thr Met Arg Val Thr Trp Ala Pro Pro Ser Ile
        1280                1285                1290
Asp Leu Thr Asn Phe Leu Val Arg Tyr Ser Pro Val Lys Asn Glu
        1295                1300                1305

-continued

```
Glu Asp Val Ala Glu Leu Ser Ile Ser Pro Ser Asp Asn Ala Val
    1310                1315                1320

Val Leu Thr Asn Leu Leu Pro Gly Thr Glu Tyr Val Val Ser Val
    1325                1330                1335

Ser Ser Val Tyr Glu Gln His Glu Ser Thr Pro Leu Arg Gly Arg
    1340                1345                1350

Gln Lys Thr Gly Leu Asp Ser Pro Thr Gly Ile Asp Phe Ser Asp
    1355                1360                1365

Ile Thr Ala Asn Ser Phe Thr Val His Trp Ile Ala Pro Arg Ala
    1370                1375                1380

Thr Ile Thr Gly Tyr Arg Ile Arg His His Pro Glu His Phe Ser
    1385                1390                1395

Gly Arg Pro Arg Glu Asp Arg Val Pro His Ser Arg Asn Ser Ile
    1400                1405                1410

Thr Leu Thr Asn Leu Thr Pro Gly Thr Glu Tyr Val Val Ser Ile
    1415                1420                1425

Val Ala Leu Asn Gly Arg Glu Glu Ser Pro Leu Leu Ile Gly Gln
    1430                1435                1440

Gln Ser Thr Val Ser Asp Val Pro Arg Asp Leu Glu Val Val Ala
    1445                1450                1455

Ala Thr Pro Thr Ser Leu Leu Ile Ser Trp Asp Ala Pro Ala Val
    1460                1465                1470

Thr Val Arg Tyr Tyr Arg Ile Thr Tyr Gly Glu Thr Gly Gly Asn
    1475                1480                1485

Ser Pro Val Gln Glu Phe Thr Val Pro Gly Ser Lys Ser Thr Ala
    1490                1495                1500

Thr Ile Ser Gly Leu Lys Pro Gly Val Asp Tyr Thr Ile Thr Val
    1505                1510                1515

Tyr Ala Val Thr Gly Arg Gly Asp Ser Pro Ala Ser Ser Lys Pro
    1520                1525                1530

Ile Ser Ile Asn Tyr Arg Thr Glu Ile Asp Lys Pro Ser Gln Met
    1535                1540                1545

Gln Val Thr Asp Val Gln Asp Asn Ser Ile Ser Val Lys Trp Leu
    1550                1555                1560

Pro Ser Ser Ser Pro Val Thr Gly Tyr Arg Val Thr Thr Thr Pro
    1565                1570                1575

Lys Asn Gly Pro Gly Pro Thr Lys Thr Lys Thr Ala Gly Pro Asp
    1580                1585                1590

Gln Thr Glu Met Thr Ile Glu Gly Leu Gln Pro Thr Val Glu Tyr
    1595                1600                1605

Val Val Ser Val Tyr Ala Gln Asn Pro Ser Gly Glu Ser Gln Pro
    1610                1615                1620

Leu Val Gln Thr Ala Val Thr Asn Ile Asp Arg Pro Lys Gly Leu
    1625                1630                1635

Ala Phe Thr Asp Val Asp Val Asp Ser Ile Lys Ile Ala Trp Glu
    1640                1645                1650

Ser Pro Gln Gly Gln Val Ser Arg Tyr Arg Val Thr Tyr Ser Ser
    1655                1660                1665

Pro Glu Asp Gly Ile His Glu Leu Phe Pro Ala Pro Asp Gly Glu
    1670                1675                1680

Glu Asp Thr Ala Glu Leu Gln Gly Leu Arg Pro Gly Ser Glu Tyr
    1685                1690                1695
```

```
Thr Val Ser Val Val Ala Leu His Asp Asp Met Glu Ser Gln Pro
    1700            1705                1710
Leu Ile Gly Thr Gln Ser Thr Ala Ile Pro Ala Pro Thr Asp Leu
    1715            1720                1725
Lys Phe Thr Gln Val Thr Pro Thr Ser Leu Ser Ala Gln Trp Thr
    1730            1735                1740
Pro Pro Asn Val Gln Leu Thr Gly Tyr Arg Val Arg Val Thr Pro
    1745            1750                1755
Lys Glu Lys Thr Gly Pro Met Lys Glu Ile Asn Leu Ala Pro Asp
    1760            1765                1770
Ser Ser Ser Val Val Val Ser Gly Leu Met Val Ala Thr Lys Tyr
    1775            1780                1785
Glu Val Ser Val Tyr Ala Leu Lys Asp Thr Leu Thr Ser Arg Pro
    1790            1795                1800
Ala Gln Gly Val Val Thr Thr Leu Glu Asn Val Ser Pro Pro Arg
    1805            1810                1815
Arg Ala Arg Val Thr Asp Ala Thr Glu Thr Thr Ile Thr Ile Ser
    1820            1825                1830
Trp Arg Thr Lys Thr Glu Thr Ile Thr Gly Phe Gln Val Asp Ala
    1835            1840                1845
Val Pro Ala Asn Gly Gln Thr Pro Ile Gln Arg Thr Ile Lys Pro
    1850            1855                1860
Asp Val Arg Ser Tyr Thr Ile Thr Gly Leu Gln Pro Gly Thr Asp
    1865            1870                1875
Tyr Lys Ile Tyr Leu Tyr Thr Leu Asn Asp Asn Ala Arg Ser Ser
    1880            1885                1890
Pro Val Val Ile Asp Ala Ser Thr Ala Ile Asp Ala Pro Ser Asn
    1895            1900                1905
Leu Arg Phe Leu Ala Thr Thr Pro Asn Ser Leu Leu Val Ser Trp
    1910            1915                1920
Gln Pro Pro Arg Ala Arg Ile Thr Gly Tyr Ile Ile Lys Tyr Glu
    1925            1930                1935
Lys Pro Gly Ser Pro Pro Arg Glu Val Val Pro Arg Pro Arg Pro
    1940            1945                1950
Gly Val Thr Glu Ala Thr Ile Thr Gly Leu Glu Pro Gly Thr Glu
    1955            1960                1965
Tyr Thr Ile Tyr Val Ile Ala Leu Lys Asn Asn Gln Lys Ser Glu
    1970            1975                1980
Pro Leu Ile Gly Arg Lys Lys Thr Asp Glu Leu Pro Gln Leu Val
    1985            1990                1995
Thr Leu Pro His Pro Asn Leu His Gly Pro Glu Ile Leu Asp Val
    2000            2005                2010
Pro Ser Thr Val Gln Lys Thr Pro Phe Val Thr His Pro Gly Tyr
    2015            2020                2025
Asp Thr Gly Asn Gly Ile Gln Leu Pro Gly Thr Ser Gly Gln Gln
    2030            2035                2040
Pro Ser Val Gly Gln Gln Met Ile Phe Glu Glu His Gly Phe Arg
    2045            2050                2055
Arg Thr Thr Pro Pro Thr Thr Ala Thr Pro Ile Arg His Arg Pro
    2060            2065                2070
Arg Pro Tyr Pro Pro Asn Val Gly Glu Glu Ile Gln Ile Gly His
    2075            2080                2085
Ile Pro Arg Glu Asp Val Asp Tyr His Leu Tyr Pro His Gly Pro
```

```
                  2090                2095                2100

Gly Leu Asn Pro Asn Ala Ser  Thr Gly Gln Glu Ala  Leu Ser Gln
            2105                 2110                 2115

Thr Thr Ile Ser Trp Ala Pro  Phe Gln Asp Thr Ser  Glu Tyr Ile
    2120                 2125                 2130

Ile Ser Cys His Pro Val Gly  Thr Asp Glu Glu Pro  Leu Gln Phe
        2135                 2140             2145

Arg Val Pro Gly Thr Ser Thr  Ser Ala Thr Leu Thr  Gly Leu Thr
    2150                 2155                 2160

Arg Gly Ala Thr Tyr Asn Ile  Ile Val Glu Ala Leu  Lys Asp Gln
    2165                 2170                 2175

Gln Arg His Lys Val Arg Glu  Glu Val Val Thr Val  Gly Asn Ser
    2180                 2185                 2190

Val Asn Glu Gly Leu Asn Gln  Pro Thr Asp Asp Ser  Cys Phe Asp
    2195                 2200                 2205

Pro Tyr Thr Val Ser His Tyr  Ala Val Gly Asp Glu  Trp Glu Arg
    2210                 2215                 2220

Met Ser Glu Ser Gly Phe Lys  Leu Leu Cys Gln Cys  Leu Gly Phe
    2225                 2230                 2235

Gly Ser Gly His Phe Arg Cys  Asp Ser Ser Arg Trp  Cys His Asp
    2240                 2245                 2250

Asn Gly Val Asn Tyr Lys Ile  Gly Glu Lys Trp Asp  Arg Gln Gly
    2255                 2260                 2265

Glu Asn Gly Gln Met Met Ser  Cys Thr Cys Leu Gly  Asn Gly Lys
    2270                 2275                 2280

Gly Glu Phe Lys Cys Asp Pro  His Glu Ala Thr Cys  Tyr Asp Asp
    2285                 2290                 2295

Gly Lys Thr Tyr His Val Gly  Glu Gln Trp Gln Lys  Glu Tyr Leu
    2300                 2305                 2310

Gly Ala Ile Cys Ser Cys Thr  Cys Phe Gly Gly Gln  Arg Gly Trp
    2315                 2320                 2325

Arg Cys Asp Asn Cys Arg Arg  Pro Gly Gly Glu Pro  Ser Pro Glu
    2330                 2335                 2340

Gly Thr Thr Gly Gln Ser Tyr  Asn Gln Tyr Ser Gln  Arg Tyr His
    2345                 2350                 2355

Gln Arg Thr Asn Thr Asn Val  Asn Cys Pro Ile Glu  Cys Phe Met
    2360                 2365                 2370

Pro Leu Asp Val Gln Ala Asp  Arg Glu Asp Ser Arg  Glu
    2375                 2380                 2385

<210> SEQ ID NO 2
<211> LENGTH: 70
<212> TYPE: PRT
<213> ORGANISM: Homo sapiens

<400> SEQUENCE: 2

Gly Pro Glu Thr Leu Cys Gly  Ala Glu Leu Val Asp  Ala Leu Gln Phe
1               5                        10                    15

Val Cys Gly Asp Arg Gly Phe  Tyr Phe Asn Lys Pro  Thr Gly Tyr Gly
            20                       25                    30

Ser Ser Ser Arg Arg Ala Pro  Gln Thr Gly Ile Val  Asp Glu Cys Cys
        35                        40                    45

Phe Arg Ser Cys Asp Leu Arg  Arg Leu Glu Met Tyr  Cys Ala Pro Leu
    50                       55                    60
```

Lys Pro Ala Lys Ser Ala
65              70

<210> SEQ ID NO 3
<211> LENGTH: 67
<212> TYPE: PRT
<213> ORGANISM: Homo sapiens

<400> SEQUENCE: 3

Ala Tyr Arg Pro Ser Glu Thr Leu Cys Gly Gly Glu Leu Val Asp Thr
1               5                   10                  15

Leu Gln Phe Val Cys Gly Asp Arg Gly Phe Tyr Phe Ser Arg Pro Ala
            20                  25                  30

Ser Arg Val Ser Arg Arg Ser Arg Gly Ile Val Glu Glu Cys Cys Phe
        35                  40                  45

Arg Ser Cys Asp Leu Ala Leu Leu Glu Thr Tyr Cys Ala Thr Pro Ala
    50                  55                  60

Lys Ser Glu
65

<210> SEQ ID NO 4
<211> LENGTH: 53
<212> TYPE: PRT
<213> ORGANISM: Homo sapiens

<400> SEQUENCE: 4

Asn Ser Asp Ser Glu Cys Pro Leu Ser His Asp Gly Tyr Cys Leu His
1               5                   10                  15

Asp Gly Val Cys Met Tyr Ile Glu Ala Leu Asp Lys Tyr Ala Cys Asn
            20                  25                  30

Cys Val Val Gly Tyr Ile Gly Glu Arg Cys Gln Tyr Arg Asp Leu Lys
        35                  40                  45

Trp Trp Glu Leu Arg
    50

<210> SEQ ID NO 5
<211> LENGTH: 146
<212> TYPE: PRT
<213> ORGANISM: Homo sapiens

<400> SEQUENCE: 5

Pro Ala Leu Pro Glu Asp Gly Gly Ser Gly Ala Phe Pro Pro Gly His
1               5                   10                  15

Phe Lys Asp Pro Lys Arg Leu Tyr Cys Lys Asn Gly Gly Phe Phe Leu
            20                  25                  30

Arg Ile His Pro Asp Gly Arg Val Asp Gly Val Arg Glu Lys Ser Asp
        35                  40                  45

Pro His Ile Lys Leu Gln Leu Gln Ala Glu Glu Arg Gly Val Val Ser
    50                  55                  60

Ile Lys Gly Val Cys Ala Asn Arg Tyr Leu Ala Met Lys Glu Asp Gly
65                  70                  75                  80

Arg Leu Leu Ala Ser Lys Cys Val Thr Asp Glu Cys Phe Phe Phe Glu
                85                  90                  95

Arg Leu Glu Ser Asn Asn Tyr Asn Thr Tyr Arg Ser Arg Lys Tyr Thr
            100                 105                 110

Ser Trp Tyr Val Ala Leu Lys Arg Thr Gly Gln Tyr Lys Leu Gly Ser
        115                 120                 125

Lys Thr Gly Pro Gly Gln Lys Ala Ile Leu Phe Leu Pro Met Ser Ala

Lys Ser
145

<210> SEQ ID NO 6
<211> LENGTH: 162
<212> TYPE: PRT
<213> ORGANISM: Homo sapiens

<400> SEQUENCE: 6

Cys Asn Asp Met Thr Pro Glu Gln Met Ala Thr Asn Val Asn Cys Ser
1               5                   10                  15
Ser Pro Glu Arg His Thr Arg Ser Tyr Asp Tyr Met Glu Gly Gly Asp
            20                  25                  30
Ile Arg Val Arg Arg Leu Phe Cys Arg Thr Gln Trp Leu Arg Ile Asp
        35                  40                  45
Lys Arg Gly Lys Val Lys Gly Thr Gln Glu Met Lys Asn Asn Tyr Asn
    50                  55                  60
Ile Met Glu Ile Arg Thr Val Ala Val Gly Ile Val Ala Ile Lys Gly
65                  70                  75                  80
Val Glu Ser Glu Phe Tyr Leu Ala Met Asn Lys Glu Gly Lys Leu Tyr
                85                  90                  95
Ala Lys Lys Glu Cys Asn Glu Asp Cys Asn Phe Lys Glu Leu Ile Leu
            100                 105                 110
Glu Asn His Tyr Asn Thr Tyr Ala Ser Ala Lys Trp Thr His Asn Gly
        115                 120                 125
Gly Glu Met Phe Val Ala Leu Asn Gln Lys Gly Ile Pro Val Arg Gly
    130                 135                 140
Lys Lys Thr Lys Lys Glu Gln Lys Thr Ala His Phe Leu Pro Met Ala
145                 150                 155                 160
Ile Thr

<210> SEQ ID NO 7
<211> LENGTH: 5
<212> TYPE: PRT
<213> ORGANISM: Homo sapiens

<400> SEQUENCE: 7

Gly Gly Gly Gly Ser
1               5

<210> SEQ ID NO 8
<211> LENGTH: 7
<212> TYPE: PRT
<213> ORGANISM: Homo sapiens

<400> SEQUENCE: 8

Gly Gly Gly Gly Ser Ser Ser
1               5

<210> SEQ ID NO 9
<211> LENGTH: 15
<212> TYPE: PRT
<213> ORGANISM: Homo sapiens

<400> SEQUENCE: 9

Gly Gly Gly Gly Ser Gly Gly Gly Ser Gly Gly Gly Gly Ser
1               5                   10                  15

```
<210> SEQ ID NO 10
<211> LENGTH: 20
<212> TYPE: PRT
<213> ORGANISM: Homo sapiens

<400> SEQUENCE: 10

Gly Gly Gly Gly Ser Gly Gly Gly Gly Ser Gly Gly Gly Gly Ser Gly
1               5                   10                  15

Gly Gly Gly Ser
            20

<210> SEQ ID NO 11
<211> LENGTH: 6
<212> TYPE: PRT
<213> ORGANISM: Homo sapiens

<400> SEQUENCE: 11

Leu Ile Lys Met Lys Pro
1               5

<210> SEQ ID NO 12
<211> LENGTH: 7
<212> TYPE: PRT
<213> ORGANISM: Homo sapiens

<400> SEQUENCE: 12

Gln Pro Gln Gly Leu Ala Lys
1               5
```

FIBRONECTIN: GROWTH FACTOR CHIMERAS

CROSS-REFERENCE TO RELATED APPLICATIONS

The present invention is a U.S. National Stage under 35 USC 371 patent application, claiming priority to Serial No. PCT/AU2010/001613, filed on 30 Nov. 2010, which claims priority from U.S. patent application Ser Nos. 12/627,647, filed on 30 Nov. 2009 and 12/793,386, filed on 3 Jun. 2010, the entirety of all which are incorporated herein.

FIELD OF THE INVENTION

THIS INVENTION relates to protein complexes having respective domains that enable binding to and activation of both a growth factor receptor and an integrin receptor for fibronectin. In particular embodiments, this invention relates to chimeric proteins comprising growth factors such as insulin-like growth factor-I (IGF-I), insulin-like growth factor-II (IGF-II), epidermal growth factor (EGF), basic fibroblast growth factor (bFGF), or keratinocyte growth factor (KGF) receptor-binding domains and an integrin receptor-binding domain of fibronectin (FN). More particularly, this invention relates to protein complexes that stimulate cell migration and to compositions and methods that promote or induce cell migration and/or proliferation. These compositions and methods have use in wound healing, tissue engineering, cosmetic and therapeutic treatments such as skin replacement, and skin replenishment and treatment of burns where epithelial cell migration and/or proliferation is required. In other embodiments, the invention provides treatment provided by the present invention related to prevention or inhibition of cancer cell metastasis, particularly in relation to breast cancer.

BACKGROUND OF THE INVENTION

A number of peptide growth factors involved in a broad range of cellular processes including hyperplasia, DNA synthesis, differentiation, cell cycle progression, and inhibition of apoptosis are known, and include the insulin-like growth factors (IGFs, e.g., IGF-I and IGF-II) (Jones & Clemmons, 1995, Endocrine Rev. 16 3; Wood & Yee, 2000, J. Mammary Gland Biology and Neoplasia 5 1), EGF (Heldin et al., 1981, Science 4 1122), bFGF (Taraboletti et al., 1997, Cell Growth. Differ. 8 471), and KGF (Marchese et al., 1990, J. Cell Physiol. 144 326). These effects are mediated through binding to their cognate tyrosine-kinase linked cell surface receptors, the type 1 IGF receptor (IGF-IR), EGF receptor, bFGF receptor, and KGF receptor, respectively. The IGFs are also tightly regulated by a family of specific binding proteins, termed IGFBPs, whose primary role is to bind free IGFs and thereby moderate their half-life, specificity and activity (Clemmons, 1998, Mol. Cell. Endoerinol. 140 19).

Fibronectin is a high molecular mass adhesive glycoprotein found in all vertebrates. Fibronectin plays a role in cell adhesion, cell morphology and surface architecture. It's main function seems to be its involvement in cellular migration during development, tissue repair and wound healing, regulation of cell growth, and differentiation (Alitalo & Vaheri, 1982, Adv. Cancer Res. 37 111; Yamada, 1983, Annu. Rev. Biochem. 62 761; Hynes, 1985, Annu. Rev. Cell Biol. 1 67). Fibronectin polymorphism is due to alternative splicing patterns in three regions (ED-A, ED-B and IIICS) of the single fibronectin primary transcript (Petersen et al., 1983, Proc. Natl. Acad. Sci. USA 80 137; Schwarzbauer et al., 1983, Cell 35 421; Kornblihtt et al., 1984, Nucleic Acids Res. 12 5853). The exact composition of fibronectin depends on the tissue type and/or cellular conditions. In humans, there are potentially 20 different forms of fibronectin, most arising from alternative splicing of some type 3 modules (Potts and Campbell, 1994, Curr. Opin. Cell Biol. 6 648). Expression of fibronectin splicing variants appears to be both developmentally regulated and tissue-specific.

Fibronectin has the ability to bind a number of extracellular molecules, including heparin, collagen and hyaluronic acid. Fibronectin organizes cell-cell interactions and cellular interaction with the extracellular matrix by binding to different components of the extracellular matrix and to membrane-bound fibronectin receptors (integrins) on cell surfaces.

However, the relative contributions of growth factors and fibronectin, and their respective domains, present in protein complexes, in terms of stimulating biological responses such as cell migration and/or proliferation, have remained elusive.

SUMMARY OF THE INVENTION

The present inventors have discovered that protein complexes in the form of synthetic chimeras comprising growth factors such as IGF-I, IGF-II, EGF, bFGF, or KGF and FN stimulate cell migration and/or proliferation by binding and synergistically co-activating cognate growth factor receptors and FN-binding integrin receptors.

Therefore, the invention is broadly directed to isolated protein complexes that comprise a receptor-binding domain of a growth factor domain and at least a domain of fibronectin that is capable of binding an integrin receptor, wherein the isolated protein complex can co-activate the growth factor and integrin receptor to thereby elicit a biological response.

In a first aspect, the invention provides an isolated protein complex in the form of a synthetic chimeric protein comprising an amino acid sequence of:

(i) a growth factor, or at least a domain of a growth factor which is capable of binding a cognate growth factor receptor; and (ii) fibronectin, or a fragment of fibronectin comprising at least an integrin-binding domain of fibronectin.

Preferably, according to the aforementioned aspects the growth factor is TGF-I, IGF-II, EGF, bFGF, or KGF.

Preferably, the integrin receptor is an $\alpha_1$ or an $\alpha_4$ integrin.

This aspect of the invention also contemplates an amino acid sequence of one or more additional fragments of fibronectin in the synthetic chimeric protein.

This aspect of the invention also includes within its scope amino acid deletions, additions, substitutions and/or mutations of amino acid sequences corresponding to (i) and (ii) above, as well as amino acid sequences corresponding to the one or more additional fragments of fibronectin.

In a second aspect, the invention provides an isolated nucleic acid encoding the isolated protein complex of the first aspect.

In a third aspect, the invention provides a genetic construct comprising the isolated nucleic acid of the second aspect operably linked to one or more regulatory sequences in an expression vector.

Preferably, the genetic construct is an expression construct.

In a fourth aspect, the invention provides a host cell comprising the genetic construct of the third aspect.

In a fifth aspect, the invention provides a pharmaceutical composition comprising the isolated protein complex of the first aspect and a pharmaceutically-acceptable carrier, diluent or excipient.

This aspect of the invention also contemplates a pharmaceutical composition comprising the host cell of the fourth aspect, which cell expresses said synthetic protein(s).

In a sixth aspect, the invention provides an antibody specific for the synthetic protein of the first aspect.

In a seventh aspect, the invention provides a method of promoting cell migration including the step of using a synthetic protein to bind both a growth factor receptor and an integrin receptor.

Preferably, the growth factor receptor is IGF-IR, EGF receptor, bFGF receptor, or KGF receptor.

Preferably, the integrin receptor is an $\alpha_1$ or an $\alpha_4$ integrin.

In a preferred embodiment, this aspect of the invention relates to promotion or induction of epithelial/keratinocyte/fibroblast cell migration and/or proliferation to facilitate wound healing in mammals, preferably humans.

Preferably, said synthetic protein is as according to the first aspect of the invention.

In an eighth aspect, the invention provides a method of preventing cell migration and/or proliferation, including the step of preventing, inhibiting or otherwise reducing binding of both a growth factor receptor and an integrin receptor by a complex comprising a growth factor and fibronectin.

Preferably, the growth factor receptor is IGF-IR, EGF receptor, bFGF receptor, or KGF receptor.

Preferably, the integrin receptor is an $\alpha_1$ or an $\alpha_4$ integrin.

In a preferred embodiment, this aspect of the invention relates to prevention or inhibition of metastatic cancer cell migration and/or proliferation in mammals, preferably humans.

A particular example contemplated by this aspect of the invention is prevention or inhibition of breast cancer metastasis.

It will also be appreciated that the methods of the seventh and eighth aspects may encompass prophylactic and therapeutic methods of treatment.

In a ninth aspect, the invention provides use of the isolated protein complex of the first aspect to produce a molecule that:
 (i) is an agonist of protein complexes comprising a growth factor and fibronectin; or
 (ii) is an antagonist of protein complexes comprising a growth factor and
fibronectin.

In one embodiment, the invention provides use of the synthetic protein of the first aspect to produce a molecule that:
 (i) is an agonist of GF-I:FN, IGF-II:FN, EGF:FN, bFGF:FN, KGF:FN,
or IGF-I:IGFBP:FN protein complexes; or
 (ii) is an antagonist of IGF-I:FN, IGF-II:FN, EGF:FN, bFGF:FN,
KGF:FN, or IGF-I:IGFBP:FN protein complexes.

Agonists and/or antagonists produced according to this aspect of the invention may have particular efficacy in promoting wound healing, tissue engineering, skin regeneration and/or prevention of cancer cell metastasis or hyperproliferative disorders of the skin, such as scarring and psoriasis.

In a tenth aspect, the invention provides a biomaterial that comprises the isolated protein complex of the first aspect.

In particular embodiments the biomaterial may be a surgical implant, prosthesis, scaffold, wound or burn dressing, or the like suitably impregnated, coated or otherwise comprising an isolated protein complex of the invention.

BRIEF DESCRIPTION OF THE FIGURES

FIG. 1. Amino acid sequence of (A) human fibronectin (SEQ ID NO:1), (B) mature IGF-I (SEQ ID NO:2), (C) mature IGF-II (SEQ ID NO:3), (D) mature EGF (SEQ ID NO:4), (E) mature bFGF (SEQ ID NO:5), (F) mature KGF (SEQ ID NO:6), and (G) preferred linker sequences (SEQ ID NOs:7-12).

DETAILED DESCRIPTION OF THE INVENTION

Figure 2:
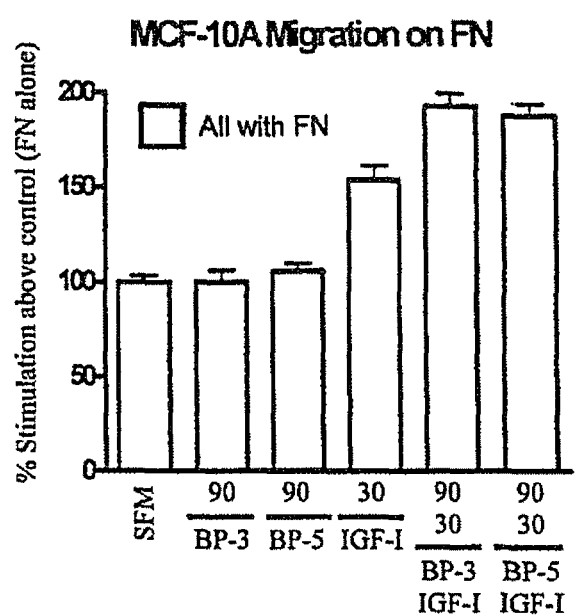
FIG. 2. IGF-I, IGFBP and FN protein complexes stimulate breast cancer cell migration. MCF-10A cells were seeded onto Transwells that had been coated with FN (1 µg/mL) and increasing concentrations of IGF-I prebound in the presence of IGFBP-3 or -5. The cells where allowed to migrate for 5 hours. The number of cells traversing the membrane in response to each treatment was then expressed as a percentage of those that migrated on FN only (SFM). MCF-10 data are pooled from three experiments with treatments tested in four wells in each replicate experiment. Error bars indicate SEM. SFM=Serum-free media.

The present invention has arisen from the discovery that synthetic chimeras comprising growth factors such as IGF-I, IGF-II, EGF, bFGF, or KGF and FN bind and exert their biological effect on cell migration through their cognate growth factor receptors and the FN-binding integrin receptor expressed by responsive cells. More particularly, this dual binding event synergistically stimulates cell migration and/or proliferation. These stable, biologically active single-chain chimeric molecules comprise at least the minimal domain or region of a growth factor capable of binding its cognate receptor in combination with one or more type-III domains of FN comprising at least an integrin-binding domain of FN.

This discovery has led the present inventors to provide an isolated protein complex that comprises at least the minimal domain or region of IGF-I, IGF-II, EGF, bFGF, or KGF, for example, capable of binding their cognate receptors in combination with the integrin-binding domain of FN. Even more particularly, a single, contiguous protein may be produced which comprises these domains.

Such protein complexes, in the form of a single synthetic protein, coordinately bind or co-ligate their cognate receptors and the FN-binding integrin receptor and are therefore useful agents for the promotion of cell migration and/or proliferation and wound healing. Analogously, prevention of cognate receptor and FN-binding integrin receptor co-ligation can be used to prevent cancer cell metastasis.

Throughout this specification, unless otherwise indicated, "comprise", "comprises" and "comprising" are used inclusively rather than exclusively, so that a stated integer or group of integers may include one or more other non-stated integers or groups of integers.

In the particular context of growth factor receptor-binding domains and integrin-binding domains, such a domain will comprise an amino acid sequence of the domain, together with other, additional amino acids as desired.

It will be understood also that such a domain may "consist essentially of" the amino acid sequence of the domain, together with no more than ten, preferably no more than five or even more preferably no more than four, three, two, or one additional amino acids.

It will be understood also that such a domain may "consist of" the amino acid sequence of the domain, in the absence of any additional amino acids.

For the purposes of this invention, by "isolated" is meant material that has been removed from its natural state or otherwise been subjected to human manipulation. Isolated material may be substantially or essentially free from components that normally accompany it in its natural state, or may be manipulated so as to be in an artificial state together with components that normally accompany it in its natural state. Isolated material may be in native, chemical synthetic or recombinant form.

As used herein, by "synthetic" is meant not naturally occurring but made through human technical intervention. In the context of synthetic proteins and nucleic acids, this encompasses molecules produced by recombinant, chemical synthetic or combinatorial techniques as are well understood in the art.

By "protein" is meant an amino acid polymer. The amino acids may be natural or non-natural amino acids, D- or L-amino acids as are well understood in the art. The term "protein" also includes and encompasses such terms as "glycoprotein", "lipoprotein" and the like, as are commonly used in the art.

A "peptide" is a protein having less than fifty (50) amino acids.

A "polypeptide" is a protein having fifty (50) or more amino acids.

As hereinbefore described, the present invention provides, in one particular aspect, an isolated protein complex in the form of a synthetic chimeric protein comprising an amino acid sequence of:

(i) a growth factor, or at least a domain of a growth factor which is capable of binding a cognate growth factor receptor; and (ii) fibronectin, or a fragment of fibronectin comprising at least an integrin-binding domain of fibronectin.

As used herein, a "chimeric protein", comprises a contiguous sequence of amino acids, the amino acids derived from an integrin receptor-binding domain of fibronectin, optionally, additional domains of fibronectin, and a growth factor or at least a receptor-binding domain of a growth factor.

As used herein, a "growth factor" is a biologically active protein that is capable of regulating cell growth, differentiation, survival and/or migration in vitro and/or in vivo.

Exemplary growth factors include, but are not limited to, IGFs (Jones & Clemmons, 1995, Endocrine Rev. 16 3; Wood & Yee, 2000, J. Mammary Gland Biology and Neoplasia 5 1; Keiss et al., 1994, Hormone Research 41 66), such as IGF-I (UniProtKB/Swiss-Prot: #PO5019, mature protein comprises amino acid residues 49-118 of the complete sequence) and IGF-II (UniProtKB/Swiss-Prot: #P01344, mature protein comprises amino acid residues 25-91 of the complete sequence), VEGF (Neufeld et al., 1999, FASEB J. 13 9-22), PDGF (Heldin, 1992, EMBO J. 11 4251-4259), EGF (Heldin et al., 1981, Science 4 1122-1123; UniProtKB/Swiss-Prot: #P01133, mature protein comprises amino acid residues 971-1023 of the complete sequence), fibroblast growth factor (FGF; Nurcombe et al., 2000, J. Biol. Chem. 275 30009-30018), bFGF (Taraboletti et al., 1997, Cell Growth. Differ. 8 471-479; UniProtKB/Swiss-Prot: #P09038, mature protein comprises amino acid residues 143-288 of the complete sequence), osteopontin (Nam et al., 2000, Endocrinol. 141 1100), thrombospondin-1 (Nam et al., 2000, supra), tenascin-C (Arai et al., 1996, J. Biol. Chem. 271 6099), PAI-1 (Nam et al., 1997, Endocrinol. 138 2972), plasminogen (Campbell et al., 1998, Am. J. Physiol. 275 E321), fibrinogen (Campbell et al., 1999, J. Biol. Chem. 274 30215), fibrin (Campbell et al., 1999, supra), transferrin (Weinzimer et al., 2001, J. Clin. Endocrinol. Metab. 86 1806), and KGF (Marchese et al., 1990, J. Cell Physiol. 144 326-32; UniProtKB/Swiss-Prot: #P21781, mature protein comprises amino acid residues 32-194 of the complete sequence).

Isolated protein complexes in the form of synthetic chimeric proteins of the invention comprise a growth factor or at least a domain of a growth factor of a growth factor which is capable of binding a cognate growth factor receptor.

In this context, by "domain" is meant at least that portion or region of a growth factor that is capable of binding a cognate growth factor receptor. Typically, although not exclusively, the cognate growth factor receptor is expressed by a cell and binding or ligation of said cognate growth factor receptor by said at least a domain of a growth factor elicits a cellular response such as cell growth, differentiation, survival and/or migration.

With particular regard to IGF-I, said domain suitably comprises amino acid residue 24, which is not a leucine residue.

Typically, said residue is tyrosine.

With particular regard to IGF-II, said domain suitably comprises amino acid residue 27, which is not a leucine residue.

Typically, said residue is tyrosine.

With particular regard to IGF-I, in one embodiment said domain consists of residues 1 to 70 of IGF-I.

In another embodiment, said domain consists of residues 4 to 70 of IGF-I.

It will also be understood that another component of isolated protein complexes of the invention is at least an integrin-binding domain of fibronectin.

Preferably, the integrin receptor is an $\alpha_1$ or an $\alpha_4$ integrin.

Although not wishing to be bound by any particular theory, it is proposed that synthetic chimeric proteins are able to co-ligate and co-activate a cognate receptor for said growth factor and an integrin receptor for fibronectin to thereby stimulate, induce, augment, or otherwise promote cell migration.

An advantage of chimeric proteins according to the invention is that they are readily produced by chemical synthetic or recombinant means and are expected to be more stable in vivo, as they do not rely on maintaining the protein-protein interactions that are required in non-covalently associated oligo-protein complexes.

In this regard, although isolated protein complexes that comprise receptor-binding domains of IGF-I would also comprise an IGFBP, it is proposed that according to the aforementioned mode of action, an IGFBP is preferably not present in an IGF-I/FN synthetic chimera.

In other embodiments, the invention provides isolated protein complexes, such as in the form of synthetic chimeric proteins, comprising IGF-I, IGF-II, EGF, bFGF, or KGF and FN, or a fragment of FN that comprises at least an integrin-binding domain of FN.

Preferably, the integrin receptor is an $\alpha_1$ or an $\alpha_4$ integrin receptor.

In this context, by "fragment" is meant a domain, subsequence or portion of fibronectin. The fragment preferably constitutes less than 500, less than 400, less than 300 or more preferably about 80-280 contiguous amino acids of a mature fibronectin sequence. Multiple fragments of fibronectin are also contemplated.

The integrin-binding domain of fibronectin suitably comprises an RGD sequence. The RGD sequence is located in fibronectin type III domains 8 to 10 (amino acids 1266-1536 of the fibronectin sequence). More specifically, the RGD sequence is present in the fibronectin type III domain 10, defined by amino acids 1447-1536 of the fibronectin sequence, although secondary integrin-binding sites may be present across the larger 8 to 10 domain region.

Accordingly, in one particular embodiment, the synthetic chimera comprises a fibronectin fragment comprising an RGD sequence, wherein the fragment comprises or consists of at least 6, at least 10, at least 20, at least 50, at least 60, at least 70, at least 80, or all of amino acids 1447-1536 of a fibronectin amino acid sequence.

In another particular embodiment, the synthetic chimera comprises a fibronectin fragment comprising an RGD sequence, said fragment comprising or consisting of an amino acid sequence of at least 6, at least 10, at least 20, at least 50, at least 100, at least 150, at least 200, at least 250, at least 260, or all of amino acids 1266-1536 of a fibronectin amino acid sequence.

In yet another particular embodiment, the synthetic chimera comprises a fibronectin fragment comprising an RGD sequence according to the aforementioned embodiments, wherein said synthetic chimera further comprises at least 10, 20, 50, 100, 200, 300, 500, 800, or 1000 amino acids of a fibronectin amino acid sequence, for example N-terminal of residue 1266 and/or C-terminal of residue 1536. Thus, said synthetic chimera can include fibronectin type I and/or type II domains, such as, for example, a fibronectin fragment comprising or consisting of at least 6, at least 10, at least 20, at least 50, at least 100, at least 150, at least 200, or all of amino acids 50-273 of a fibronectin amino acid sequence.

In still another particular embodiment, the synthetic chimera comprises a fibronectin fragment comprising or consisting of an amino acid sequence of at least 6, at least 10, at least 20, at least 50, at least 100, at least 150, at least 200, at least 250, at least 300, at least 350, or all of amino acids 1173 to 1536 of a fibronectin amino acid sequence.

It will be appreciated that the foregoing fibronectin sequence numbering is made with reference to the fibronectin sequence shown in FIG. 1. This fibronectin sequence is derived from the UniProtKB Protein Database, protein accession number P02751. Fibronectin domains and regions are set forth in Table I.

Preferably, synthetic chimeras comprising fibronectin or a fragment comprising an integrin-binding domain do not comprise an IGFBP amino acid sequence.

Preferably, synthetic chimeric proteins as hereinbefore described further comprise a "linker sequence" located between and contiguous with a growth factor sequence and a fibronectin amino acid sequence.

In one embodiment, said linker sequence comprises one or more glycine residues and one or more serine residues.

Particular examples of linker sequences may be selected from; $Gly_4$ Ser (SEQ ID NO:7); $Gly_4$ $Ser_3$ (SEQ ID NO:8); $(Gly_4$ $Ser)_3$ (SEQ ID NO:9); and $(Gly_4$ $Ser)_4$ (SEQ ID NO:10), although without limitation thereto.

In another embodiment, the linker sequence includes a Plasmin Cleavage Recognition Site (Sakiyama-Elbert et al., 2001, FASEB 15 1300), such as according to the sequence:

Leu Ile Lys Met Lys Pro    (SEQ ID NO: 11)

In yet another embodiment, the linker sequence includes a Collagenase-3 Cleavage Recognition Site (Kim & Healy, 2003, Biomacromolecules 4 1214), such as according to the sequence:

Gln Pro Gln Gly Leu Ala Lys    (SEQ ID NO: 12)

The invention also extends to use of biologically-active fragments of the synthetic chimeric proteins of the invention and/or to use of biologically-active fragments of the particular growth factor receptor-binding domains and integrin-binding domains exemplified herein.

In one embodiment, said "biologically-active fragment" has no less than 10%, preferably no less than 25%, more preferably no less than 50% and even more preferably no less than 75%, 80%, 85%, 90%, or 95% of a biological activity of a protein from which it is derived.

In another embodiment, said "biologically-active fragment" has no less than 10%, preferably no less than 25%, more preferably no less than 50% and even more preferably no less than 75%, 80%, 85%, 90%, or 95% of a contiguous amino acid sequence of a protein from which it is derived.

Also contemplated are variant protein complexes of the invention.

Typically, and in relation to proteins, a "variant" protein has one or more amino acids that have been replaced by different amino acids. It is well understood in the art that some amino acids may be changed to others with broadly similar properties without changing the nature of the activity of the protein (conservative substitutions).

It will be appreciated that one or more amino acid residues of a reference sequence, such as a growth factor, receptor-binding domain of a growth factor, an integrin-binding domain of fibronectin, IGFBPs, or one or more corresponding residues present in a synthetic chimeric protein, may be modified or deleted, or additional sequences added, without substantially altering the biological activity of the isolated protein complex of the invention.

In one embodiment, a protein variant shares at least 70%, preferably at least 80% or 85% and more preferably at least 90%, 95%, 98%, or 99% sequence identity with a reference amino acid sequence.

Preferably, sequence identify is measured over at least 60%, more preferably over at least 75%, more preferably over at least 90% or more preferably over at least 95%, 98% or substantially the full length of the reference sequence.

In order to determine percent sequence identity, optimal alignment of amino acid and/or nucleotide sequences may be conducted by computerised implementations of algorithms (Geneworks program by Intelligenetics; GAP, BESTFIT, FASTA, and TFASTA in the Wisconsin Genetics Software Package Release 7.0, Genetics Computer Group, WI, USA) or by inspection and the best alignment (i.e., resulting in the highest percentage homology over the comparison window) generated by any of the various methods selected. Reference also may be made to the BLAST family of programs as for example disclosed by Altschul et al., 1997, Nucl. Acids Res. 25 3389.

In another example, "sequence identity" may be understood to mean the "match percentage" calculated by the DNASIS computer program (Version 2.5 for windows; available from Hitachi Software engineering Co., Ltd., South San Francisco, Calif., USA).

A detailed discussion of sequence analysis can be found in Unit 19.3 of CURRENT PROTOCOLS IN MOLECULAR BIOLOGY Eds. Ausubel et al. (John Wiley & Sons Inc NY, 1995-1999).

The invention also contemplates derivatives of a receptor-binding domain of a growth factor, an integrin-binding domain of fibronectin or an isolated protein complex comprising the same.

As used herein, "derivative" proteins of the invention have been altered, for example by addition, conjugation or complexing with other chemical moieties or by post-translational modification techniques as are well understood in the art "Additions" of amino acids may include fusion of the polypeptides or variants thereof with other polypeptides or proteins. The other protein may, by way of example, assist in the purification of the protein. For instance, these include a polyhistidine tag, maltose binding protein, green fluorescent protein (GFP), Protein A, or glutathione S-transferase (GST).

Other derivatives contemplated by the invention include, but are not limited to, modification to side chains, incorporation of unnatural amino acids and/or their derivatives during peptide, polypeptide or protein synthesis and the use of crosslinkers and other methods which impose conformational constraints on the polypeptides, fragments and variants of the invention. Examples of side chain modifications contemplated by the present invention include modifications of amino groups such as by acylation with acetic anhydride, acylation of amino groups with succinic anhydride and tetrahydrophthalic anhydride, amidination with methylacetimidate, carbamoylation of amino groups with cyanate, pyridoxylation of lysine with pyridoxal-5-phosphate followed by reduction with $NaBH_4$, reductive alkylation by reaction with an aldehyde followed by reduction with $NaBH_4$, and trinitrobenzylation of amino groups with 2,4,6-trinitrobenzene sulphonic acid (TNBS).

The carboxyl group may be modified by carbodiimide activation via O-acylisourea formation followed by subsequent derivitization, by way of example, to a corresponding amide.

The guanidine group of arginine residues may be modified by formation of heterocyclic condensation products with reagents such as 2,3-butanedione, phenylglyoxal and glyoxal.

Sulphydryl groups may be modified by methods such as performic acid oxidation to cysteic acid, formation of mercurial derivatives using 4-chloromercuriphenylsulphonic acid, 4-chloromercuribenzoate, 2-chloromercuri-4-nitrophenol, phenylmercury chloride, and other mercurials, formation of a mixed disulphides with other thiol compounds, reaction with maleimide, maleic anhydride or other substituted maleimide, carboxymethylation with iodoacetic acid or iodoacetamide, and carbamoylation with cyanate at alkaline pH.

Tryptophan residues may be modified, for example, by alkylation of the indole ring with 2-hydroxy-5-nitrobenzyl bromide or sulphonyl halides, or by oxidation with N-bromosuccinimide.

Tyrosine residues may be modified by nitration with tetranitromethane to form a 3-nitrotyrosine derivative.

The imidazole ring of a histidine residue may be modified by N-carbethoxylation with diethylpyrocarbonate or by alkylation with iodoacetic acid derivatives.

Examples of incorporating non-natural amino acids and derivatives during peptide synthesis include, but are not limited to, use of 4-amino butyric acid, 6-aminohexanoic acid, 4-amino-3-hydroxy-5-phenylpentanoic acid, 4-amino-3-hydroxy-6-methylheptanoic acid, t-butylglycine, norleucine, norvaline, phenylglycine, ornithine, sarcosine, 2-thienyl alanine, and/or D-isomers of amino acids.

An example of methods suitable for chemical derivatization of proteins is provided in Chapter 15 of CURRENT PROTOCOLS IN PROTEIN SCIENCE Eds. Coligan et. al., John Wiley & Sons NY (1995-2001).

Isolated protein complexes, and individual protein components thereof, (inclusive of fragments, variants, derivatives, and homologs) may be prepared by any suitable procedure known to those of skill in the art.

In one embodiment, proteins of the invention are produced by chemical synthesis. Chemical synthesis techniques are well known in the art, although the skilled person may refer to Chapter 18 of CURRENT PROTOCOLS IN PROTEIN SCIENCE Eds. Coligan et. al., John Wiley & Sons NY (1995-2001) for examples of suitable methodology.

In another embodiment, proteins may be prepared as recombinant proteins.

While production of recombinant proteins is well known in the art, the skilled person may refer to standard protocols as for example described in Sambrook et al., MOLECULAR CLONING. A Laboratory Manual (Cold Spring Harbor Press, 1989), in particular Sections 16 and 17; CURRENT PROTOCOLS IN MOLECULAR BIOLOGY Eds. Ausubel et al., (John Wiley & Sons, Inc. 1995-1999), in particular Chapters 10 and 16; and CURRENT PROTOCOLS IN PROTEIN SCIENCE Eds. Coligan et al., (John Wiley & Sons, Inc. 1995-1999), in particular Chapters 1, 5 and 6.

In one embodiment, a recombinant protein is produced by a method including the steps of:
(i) preparing an expression construct which comprises a nucleic acid encoding said protein, operably linked to one or more regulatory nucleotide sequences in an expression vector;
(ii) transfecting or transforming a host cell with the expression construct; and
(iii) expressing the recombinant protein in said host cell.

An "expression vector" may be either a self-replicating extra-chromosomal vector such as a plasmid, or a vector that integrates into a host genome.

By "operably linked" or "operably connected" is meant that said regulatory nucleotide sequence(s) is/are positioned relative to the recombinant nucleic acid of the invention to initiate, regulate or otherwise control transcription of the nucleic acid, or translation of a protein encoded by the nucleic acid.

Regulatory nucleotide sequences will generally be appropriate for the host cell used for expression. Numerous types of appropriate expression vectors and suitable regulatory sequences are known in the art for a variety of host cells.

Typically, said one or more regulatory nucleotide sequences may include, but are not limited to, promoter sequences, leader or signal sequences, ribosomal binding sites, transcriptional start and termination sequences, translational start and termination sequences, splice donor/acceptor sequences, and enhancer or activator sequences.

Constitutive promoters (such as CMV, RSV, adenovirus, SV40, and human elongation factor promoters) and inducible/repressible promoters (such as tet-repressible promoters and IPTG-, metallothionine- or ecdysone-inducible promoters) are well known in the art and are contemplated by the invention. It will also be appreciated that promoters may be hybrid promoters that combine elements of more than one promoter.

The expression construct may also include a fusion partner (typically provided by the expression vector) so that the recombinant protein of the invention is expressed as a fusion polypeptide with said fusion partner. The main advantage of fusion partners is that they assist identification and/or purification of said fusion protein.

Well known examples of fusion partners include, but are not limited to, glutathione-S-transferase (GST), Fc portion of human IgG, maltose binding protein (MBP), and hexahistidine ($HIS_6$), which are particularly useful for isolation of the fusion protein by affinity chromatography. For the purposes of fusion protein purification by affinity chromatography, relevant matrices for affinity chromatography are glutathione-, amylose-, and nickel- or cobalt-conjugated resins respectively. Many such matrices are available in "kit" form, such as the QIAexpress™ system (Qiagen) useful with ($HIS_6$) fusion partners and the Pharmacia GST purification system.

In some cases, the fusion partners also have protease cleavage sites, such as for Factor $X_a$ or Thrombin, which allow the relevant protease to partially digest the fusion protein of the invention and thereby liberate the recombinant polypeptide of the invention therefrom. The liberated protein can then be isolated from the fusion partner by subsequent chromatographic separation.

Fusion partners according to the invention also include within their scope "epitope tags", which are usually short peptide sequences for which a specific antibody is available. Well known examples of epitope tags for which specific monoclonal antibodies are readily available include c-myc, haemagglutinin and FLAG tags.

Suitable host cells for expression may be prokaryotic or eukaryotic, such as *Escherichia coli* (DH5α for example), yeast cells, Sf9 cells utilized with a baculovirus expression system, CHO cells, COS, CV-1, NIH 3T3, and 293 cells, although without limitation thereto.

Expression constructs may also include one or more selection marker nucleotide sequences that confer transformed host cell resistance to a selection agent. Selection markers useful for the purposes of selection of transformed bacteria include bla, kanR and tetR, while transformed eukaryotic cells may be selected by markers such as hygromycin, G418 and puromycin, although without limitation thereto.

With regard to introducing genetic material into host cells, the terms "transforming" and "transfecting" are used generally to describe introduction of genetic material in a host cell. There are many well known methods for introducing foreign genetic material into a host cell including, but not limited to, calcium phosphate precipitation, electroporation, delivery by lipofectamine, lipofectin and other lipophilic agents, calcium phosphate precipitation, DEAE-Dextran transfection, microparticle bombardment, microinjection, and protoplast fusion.

The invention provides an isolated nucleic acid that encodes a synthetic chimeric protein of the invention, including variants and homologs thereof.

The term "nucleic acid" as used herein designates single- or double-stranded mRNA, RNA, cRNA, RNAi, and DNA, inclusive of cDNA and genomic DNA and DNA-RNA hybrids.

A "polynucleotide" is a nucleic acid having eighty (80) or more contiguous nucleotides, while an "oligonucleotide" has less than eighty (80) contiguous nucleotides.

A "probe" may be a single or double-stranded oligonucleotide or polynucleotide, suitably labeled for the purpose of detecting complementary sequences in Northern or Southern blotting, for example.

A "primer" is usually a single-stranded oligonucleotide, preferably having 15-50 contiguous nucleotides, which is capable of annealing to a complementary nucleic acid "template" and being extended in a template-dependent fashion by the action of a DNA polymerase such as Taq polymerase, RNA-dependent DNA polymerase or Sequenase™.

Synthetic nucleic acids of the invention may be produced by chemical synthetic approaches or by recombinant methods that utilize nucleic acid sequence amplification techniques, or a combination thereof, as are well known in the art.

Chemically synthesized primers and oligonucleotides, synthesizers and associated technologies useful according to the present invention are typically available in most laboratories or may be purchased from commercial sources.

Suitable nucleic acid amplification techniques are well known to the skilled person, and include polymerase chain reaction (PCR) and ligase chain reaction (LCR) as for example described in Chapter 15 of Ausubel et al. supra; strand displacement amplification (SDA) as for example described in U.S. Pat. No. 5,422,252; rolling circle replication (RCR) as for example described in Liu et al., 1996, J. Am. Chem. Soc. 118 1587; International application WO 92/01813 and International Application WO 97119193; nucleic acid sequence-based amplification (NASBA) as for example described by Sooknanan et al., 1994, Biotechniques 17 1077; and Q-β replicase amplification as for example described by Tyagi et al., 1996, Proc. Natl. Acad. Sci. USA 93 5395, although without limitation thereto.

A preferred nucleic acid sequence amplification technique is PCR.

As used herein, an "amplification product" refers to a nucleic acid product generated by a nucleic acid amplification technique.

In producing and expressing nucleic acids of the invention, it will also be appreciated that advantage may be taken with respect to codon sequence redundancy, such that the nucleic acids exemplified herein may be readily modified without changing an amino acid sequence encoded thereby.

In particular embodiments, nucleic acids may be optimized according to preferred "codon usage" of a host cell to be used for recombinant expression, as is well known in the art. This can effectively "tailor" a nucleic acid for optimal expression in a particular organism, or cells thereof, where preferential codon usage affects protein expression.

Therefore, the invention includes synthetic nucleic acids that are homologous to the nucleic acids exemplified herein.

In one embodiment, nucleic acid homologs share at least 70%, preferably at least 80%, more preferably at least 90%, and even more preferably at least 95% sequence identity with a nucleic acid encoding any one of the synthetic chimeric protein constructs described herein.

Preferably, sequence identity is measured over at least 70%, more preferably at least 80%, even more preferably at least 90%, 95% or advantageously over substantially the full length of the encoding nucleic acid of the invention.

In another embodiment, nucleic acid homologs hybridize to a nucleic acid encoding any one of the synthetic chimeric protein constructs described herein under high stringency conditions.

"Hybridize" and "Hybridization" are used herein to denote the pairing of at least partly complementary nucleotide sequences to produce a DNA-DNA, RNA-RNA or DNA-RNA duplex. Hybridized sequences occur through base-pairing between complementary purines and pyrimidines as is well known in the art.

In this regard, it will be appreciated that modified purines (for example, inosine, methylinosine and methyladenosine) and modified pyrimidines (thiouridine and methyleytosine) may also engage in base pairing.

"Stringency" as used herein, refers to temperature and ionic strength conditions, and presence or absence of certain organic solvents and/or detergents during hybridisation. The higher the stringency, the higher will be the required level of complementarity between hybridizing nucleotide sequences.

"Stringent conditions" designates those conditions under which only nucleic acid having a high frequency of complementary bases will hybridize.

Reference herein to high stringency conditions includes and encompasses:

(i) from at least about 31% v/v to at least about 50% v/v foguamide and from at least about 0.01 M to at least about 0.15 M salt for hybridisation at 42° C., and at least about 0.01 M to at least about 0.15 M salt for washing at 42° C.;

(ii) 1% BSA, 1 mM EDTA, 0.5 M $NaHPO_4$ (pH 7.2), 7% SDS for hybridization at 65° C., and (a) 0.1×SSC, 0.1% SDS; or (b) 0.5% BSA, 1 mM EDTA, 40 mM $NaHPO_4$ (pH 7.2), 1% SDS for washing at a temperature in excess of 65° C. for about one hour; and (iii) 0.2×SSC, 0.1% SDS for washing at or above 68° C. for about 20 minutes.

In general, washing is carried out at $T_m=69.3+0.41$ (G+C) %–12° C. In general, the $T_m$ of a duplex DNA decreases by about 1° C. with every increase of 1% in the number of mismatched bases.

Notwithstanding the above, stringent conditions are well known in the art, such as described in Chapters 2.9 and 2.10 of. Ausubel et al., supra and in particular at pages 2.9.1 through 2.9.20.

The invention also contemplates antibodies against a synthetic chimeric protein of the invention, inclusive of chimeric proteins, or fragments, variants and/or derivatives thereof. Antibodies of the invention may be polyclonal or monoclonal. Well-known protocols applicable to antibody production, purification and use may be found, for example, in Chapter 2 of Coligan et al., CURRENT PROTOCOLS IN IMMUNOLOGY (John Wiley & Sons NY, 1991-1994) and Harlow, E. & Lane, D. Antibodies: A Laboratory Manual, Cold Spring Harbor, Cold Spring Harbor Laboratory, 1988.

Generally, antibodies of the invention bind to or conjugate with a polypeptide, fragment, variant or derivative of the invention. For example, the antibodies may comprise polyclonal antibodies. Such antibodies may be prepared for example by injecting a polypeptide, fragment, variant or derivative of the invention into a production species, which may include mice or rabbits, to obtain polyclonal antisera. Methods of producing polyclonal antibodies are well known to those skilled in the art. Exemplary protocols which may be used are described for example in Coligan et al., CURRENT PROTOCOLS IN IMMUNOLOGY, supra, and in Harlow & Lane, 1988, supra.

In lieu of the polyclonal antisera obtained in the production species, monoclonal antibodies may be produced using the standard method as for example, described by Köhler & Milstein (1975, Nature 256, 495), or by more recent modifications thereof as, for example, described in Coligan et al., CURRENT PROTOCOLS IN IMMUNOLOGY, supra by immortalizing spleen or other antibody producing cells derived from a production species which has been inoculated with one or more of the polypeptides, fragments, variants or derivatives of the invention.

The invention also includes within its scope antibodies which comprise Fc or Fab fragments of the polyclonal or monoclonal antibodies referred to above. Alternatively, the antibodies may comprise single chain Fv antibodies (scFvs) against the proteins of the invention. Such scFvs may be prepared, for example, in accordance with the methods described respectively in U.S. Pat. No. 5,091,513, European Patent 239,400 or the article by Winter & Milstein (1991, Nature 349 293).

Labels may be associated with the antibody or antibody fragment.

The label may be selected from a group including a chromogen, a catalyst, an enzyme, a fluorophore, a chemiluminescent molecule, a lanthanide ion such as Europium ($Eu^{34}$), a radioisotope, and a direct visual label. In the case of a direct visual label, use may be made of a colloidal metallic or non-metallic particle, a dye particle, an enzyme or a substrate, an organic polymer, a latex particle, a liposome, or other vesicle containing a signal producing substance and the like.

A large number of enzymes useful as labels are disclosed in U.S. Pat. Nos. 4,366,241, 4,843,000 and 4,849,338. Enzyme labels useful in the present invention include alkaline phosphatase, horseradish peroxidase, luciferase, b-galactosidase, glucose oxidase, lysozyme, malate dehydrogenase, and the like. The enzyme label may be used alone or in combination with a second enzyme in solution.

By way of example, the fluorophore may be fluorescein isothiocyanate (FITC), oregon green, tetramethylrhodamine isothiocyanate (TRITE), allophycocyanin (APC), and R-Phycoerythrin (RPE), although without limitation thereto.

The invention also provides pharmaceutical compositions that comprise an isolated protein complex of the invention, inclusive of variants and derivatives thereof.

Such isolated protein complex may be in any form, inclusive of synthetic chimeric proteins of the invention, although without limitation thereto.

Pharmaceutical compositions of the invention may be used to promote or otherwise facilitate cell migration, tissue regeneration and wound healing. Alternatively, pharmaceutical compositions may be administered to prevent tumour metastasis by preventing or inhibiting tumour cell migration to a secondary site.

The composition may be used in therapeutic or prophylactic treatments as required. For example, pharmaceutical compositions may be applied in the form of therapeutic or cosmetic preparations for skin repair, wound healing, healing of burns and other dermatological treatments.

In this regard, pharmaceutical compositions may be administered in association with, or as a component of, a biomaterial, biopolymer, inorganic material such as hydroxyapatite or derivates thereof, surgical implant, prosthesis, wound or burn dressing, compress, bandage, or the like suitably impregnated, coated or otherwise comprising the pharmaceutical composition.

Suitably, the pharmaceutical composition comprises an appropriate pharmaceutically-acceptable carrier, diluent or excipient.

Preferably, the pharmaceutically-acceptable carrier, diluent or excipient is suitable for administration to mammals, and more preferably, to humans.

By "pharmaceutically-acceptable carrier, diluent or excipient" is meant a solid or liquid filler, diluent or encapsulating substance that may be safely used in systemic administration. Depending upon the particular route of administration, a variety of carriers, well known in the art may be used. These carriers may be selected from a group including sugars, starches, cellulose and its derivatives, malt, gelatine, talc, calcium sulfate, vegetable oils, synthetic oils, polyols, alginic acid, phosphate buffered solutions, emulsifiers, isotonic saline and salts such as mineral acid salts including hydrochlorides, bromides and sulfates, organic acids such as acetates, propionates and malonates, and pyrogen-free water.

A useful reference describing pharmaceutically acceptable carriers, diluents and excipients is Rerun on's Pharmaceutical Sciences (Mack Publishing Co. N.J. USA, 1991).

Any safe route of administration may be employed for providing a patient with the composition of the invention. For example, oral, rectal, parenteral, sublingual, buccal, intravenous, intra-articular, intra-muscular, intra-dermal, subcutaneous, inhalational, intraocular, intraperitoneal, intracerebroventricular, transdermal, and the like may be employed.

Dosage forms include tablets, dispersions, suspensions, injections, solutions, syrups, troches, capsules, suppositories, aerosols, transdermal patches, and the like. These dosage forms may also include injecting or implanting controlled releasing devices designed specifically for this purpose or other forms of implants modified to act additionally in this fashion. Controlled release of the therapeutic agent may be effected by coating the same, for example, with hydrophobic polymers including acrylic resins, waxes, higher aliphatic alcohols, polylactic and polyglycolic acids, and certain cellulose derivatives such as hydroxypropylmethyl cellulose. In addition, the controlled release may be effected by using other polymer matrices, liposomes and/or microspheres.

The above compositions may be administered in a manner compatible with the dosage formulation, and in such amount as is pharmaceutically-effective. The dose administered to a patient, in the context of the present invention, should be sufficient to effect a beneficial response in a patient over an appropriate period of time. The quantity of agent(s) to be administered may depend on the subject to be treated, inclusive of the age, sex, weight and general health condition thereof, factors that will depend on the judgement of the practitioner.

With regard to pharmaceutical compositions for wound healing, particular reference is made to U.S. Pat. No. 5,936, 064 and International Publication WO 99/62536.

Pharmaceutical compositions of the invention may also include expression vectors such as viral vectors such as vaccinia, and viral vectors useful in gene therapy. The latter include adenovirus and adenovirus-associated viruses (AAV) such as described in Braun-Falco et al. (1999, Gene Ther. 6 432), retroviral and lentiviral vectors such as described in Buchshaeher et al. (2000, Blood 95 2499) and vectors derived from herpes simplex virus and cytomegalovirus. A general overview of viral vectors useful in endocrine gene therapy is provided in Stone et al. (2000, J. Endocrinol. 164 103).

The present invention may also utilize specific expression vectors which target gene expression to epidermal cells, such as described in U.S. Pat. No. 5,958,764 and for in vivo wound healing applications, such as described in U.S. Pat. No. 5,962, 427.

The invention provides methods of treatment using isolated protein complexes, inclusive of synthetic chimeric proteins of the invention. These methods are particularly aimed at therapeutic and/or prophylactic treatment of mammals, and more particularly, humans.

However, therapeutic uses according to the invention may also be applicable to mammals such as domestic and companion animals, performance animals such as horses, camels and greyhounds, livestock, laboratory animals and animals used as sources of cells, organs and tissues for xenotransplantation.

The invention also contemplates methods of cosmetic treatment where isolated protein complexes, inclusive of synthetic chimeric proteins of the invention, are administered to improve or enhance skin quality or skin appearance.

Such treatments may include prevention or remediation of skin disorders such as psoriasis and hypertrophic scarring that result from aberrant skin cell proliferation.

Alternatively, methods of treatment are contemplated whereby tumour metastasis is prevented or inhibited by blocking tumour cell migration to a secondary site. In addition, methods of treating cancer by blocking cell proliferation also contemplated.

In particular embodiments, therapeutic and/or prophylactic treatments may utilize an isolated protein complex, inclusive of synthetic chimeric proteins of the invention, in association with, or as a component of, a biomaterial, biopolymer, inorganic material such as fluorohydroxyapatite, surgical implant, prosthesis, wound or burn dressing, compress, bandage, or the like suitably impregnated, coated or otherwise comprising the isolated protein complex.

Such methods include administration of pharmaceutical compositions as hereinbefore defined, and may be by way of microneedle injection into specific tissue sites, such as described in U.S. Pat. No. 6,090,790, topical creams, lotions or sealant dressings, applied to wounds, burns or ulcers, such as described in U.S. Pat. No. 6,054,122 or implants which release the composition such as described in International Publication WO 99/47070.

Gene therapy is also applicable in this regard, such as according to methods set forth in U.S. Pat. No. 5,929,040 and U.S. Pat. No. 5,962,427.

There also exist methods by which skin cells can be genetically modified for the purpose of creating skin substitutes, such as by genetically engineering desired growth factor expression (Supp et al., 2000, J. Invest. Dermatol. 114 5). An example of a review of this field is provided in Bevan et al. (Biotechnol. Gent. Eng. Rev. 16 231).

Also contemplated is "seeding" a recipient with transfected or transformed cells, such as described in International Publication WO 99/11789.

These methods can be used to stimulate cell migration and thereby facilitate or progress wound and burn healing, repair of skin lesions such as ulcers, tissue replacement and grafting such as by in vitro culturing of autologous skin, re-epithelialization of internal organs such as kidney and lung and repair of damaged nerve tissue.

Skin replacement therapy has become well known in the art, and may employ use of co-cultured epithelial/keratinocyte cell lines, for example as described in Kehe et al. (1999, Arch. Deimatol. Res. 291 600) or in vitro culture of primary (usually autologous) epidermal, dermal and/or keratinocyte cells. These techniques may also utilize engineered biomaterials and synthetic polymer "scaffolds".

Examples of reviews of the field in general are provided in Terskikh & Vasiliev (1999, Int. Rev. Cytol. 188 41) and Eaglestein & Falanga (1998, Cutis 62 1).

More particularly, the production of replacement oral mucosa useful in craniofacial surgery is described in Izumi et al. (2000, J. Dent. Res. 79 798). Fetal keratinocytes and dermal fibroblasts can be expanded in vitro to produce skin for grafting to treat skin lesions, such as described in Fauza et al. (J. Pediatr. Surg. 33 357), while skin substitutes from dermal and epidermal skin elements cultured in vitro on hyaluronic acid-derived biomaterials have been shown to be potentially useful in the treatment of burns (Zacchi et al., 1998, J. Biomed. Mater. Res. 40 187).

Polymer scaffolds are also contemplated for the purpose of facilitating replacement skin engineering, as for example described in Sheridan et al. (2000, J. Control Release 14 91) and Fauza et al. (1998, supra), as are microspheres as agents for the delivery of skin cells to wounds and burns (LaFrance & Armstrong, 1999, Tissue Eng. 5 153).

The invention contemplates use of isolated protein complexes, inclusive of synthetic chimeric proteins of the invention, to identify, screen, design or otherwise produce agonists or antagonists of complexes comprising a growth factor and fibronectin, such as IGF-I:FN, EGF:FN, bFGF:FN, KGF:FN, or IGF-I:IGFBP:FN complexes. Such agents may be a "mimetic". The term "mimetic" is used herein to refer to molecules that are designed to resemble particular functional regions of proteins or peptides, and includes within its scope the terms "agonist", "analogue" and "antagonist" as are well understood in the art.

In one embodiment, agonists are produced that mimic the binding of the cognate growth factor receptors and FN receptors by IGF-I:FN, IGF-II:FN, EGF:FN, bFGF:FN, KGF:FN, or IGF-I:IGFBP:FN complexes. Such molecules may have utility as stimulators of cell migration such as required for wound healing, skin regeneration and the like.

In another embodiment, antagonists are produced that prevent or inhibit the binding of the cognate growth factor receptors and integrin receptors by IGF-I:FN, IGF-II:FN, EGF:FN, bFGF:FN, KGF:FN, or IGFII:IGFBP:FN complexes. Such molecules may have utility as inhibitors of cell migration and/or cell proliferation and thereby constitute useful antitumour agents and also in treatments of skin disorders such as psoriasis and hypertrophic scarring that result from aberrant cell proliferation.

The aforementioned mimetics, agonists, antagonists, and analogues may be peptides, polypeptides or other organic molecules, preferably small organic molecules, with a desired biological activity and half-life.

Computer-assisted structural database searching is becoming increasingly utilized as a procedure for identifying mimetics. Database searching methods which, in principle, may be suitable for identifying mimetics, may be found in International Publication WO 94/18232 (directed to producing HIV antigen mimetics), U.S. Pat. No. 5,752,019 and International Publication WO 97/41526 (directed to identifying EPO mimetics).

Other methods include a variety of biophysical techniques which identify molecular interactions. These allow for the screening of candidate molecules according to whether said candidate molecule affects formation of IGF-I:FN, IGF-II: FN, EGF:FN, bFGF:FN, KGF:FN, or IGF-IGFBP-FN complexes, for example. Methods applicable to potentially useful techniques such as competitive radioligand binding assays (see, Upton et al., 1999, supra for a relevant method), analytical ultracentrifugation, microcalorimetry, surface plasmon resonance, and optical biosensor-based methods are provided in Chapter 20 of CURRENT PROTOCOLS IN PROTEIN SCIENCE Eds. Coligan et al., (John Wiley & Sons, 1997).

So that the present invention may be more readily understood and put into practical effect, the skilled person is referred to the following non-limiting examples.

EXAMPLES

Example 1

IGF-I, IGFBPs and FN Stimulate Cell Migration

MCF-10A cells were seeded onto Transwells that had been coated with FN (1 ug/mL) and increasing concentrations of IGF-I prebound in the presence of IGFBP-3 or -5. The cells where allowed to migrate for 5 hours. The number of cells traversing the membrane in response to each treatment was then expressed as a percentage of those that migrated on FN only (SFM). MCF-10 data are pooled from three experiments with treatments tested in four wells in each replicate experiment and shown in FIG. 2. Error bars indicate SEM. SFM=Serum-free media. IGF-I:FN, IGF-I:IGFBP-3:FN and IGF-I:IGFBP-5:FN were able to stimulate significantly increased migration above that of FN alone control wells (responses of 153.7+/−7.3%, 192.5+/−6.8% and 187.5+/−6.5% of the FN control wells, respectively) ($p<0.05$). The response of the MCF7-10A cells to IGF-I:IGFBP-3:FN and IGF-I:IGFBP-5:FN treatments was also significantly greater than those obtained with either IGFBP or IGF-I alone with FN ($p<0.05$). This data indicates that maximal responses occur when the trimeric IGF-I:IGFBP-3/5:FN complexes are present. This suggests that chimeras containing IGF-I linked to FN activate the FN binding integrins and the cognate growth factor receptor.

Example 2

Synthetic Chimeric Fibronectin:Growth Factor Proteins

Provided herein are examples of synthetic chimeric proteins of the invention, in the form of FN:growth factor (e.g., IGF-I, IGF-II, EGF, bFGF, and KGF) chimeras.

The synthetic chimeric proteins include any full-length or truncated forms of FN fused with a growth factor, with or without amino acid residue modifications. In addition, FN and the growth factors may be fused with or without the various peptide linkers.

A series of chimeric expression constructs are designed in which various lengths of the FN protein are linked to the full-length mature IGF-I, IGF-II, EGF, bFGF, or KGF proteins, or at least a domain of the IGF-I, IGF-H, EGF, bFGF, or KGF proteins capable of binding a cognate growth factor receptor. In each case, the FN segments are preferably linked to the IGF-I, IGF-II, EGF, bFGF, or KGF sequence via a linker, for example, a $Gly_4$ Ser (SEQ ID NO:7) linker, a $Gly_4 Ser_3$ (SEQ ID NO:8) linker, a $(Gly_4 Ser)_3$ (SEQ ID NO:9) linker, or a $(Gly_4 Ser)_4$ (SEQ ID NO:10) linker.

Exemplary synthetic chimeric proteins include, but are not limited to:

A) FN type-III Domain 8 [Linker] Growth Factor (IGF-I, IGF-II, EGF, bFGF, or KGF);

B) FN type-III Domains 8-9 [Linker] Growth Factor (IGF-I, IGF-II, EGF, bFGF, or KGF);

C) FN type-III Domains 8-10 [Linker] Growth Factor (IGF-I, IGF-H, EGF, bFGF, or KGF);

D) FN type-III Domain 9 [Linker] Growth Factor (IGF-I, IGF-II, EGF, bFGF, or KGF);

E) FN type-III Domains 9-10 [Linker] Growth Factor (IGF-I, IGF-II, EGF, bFGF, or KGF);

F) FN type-III Domain 10 [Linker] Growth Factor (IGF-I, IGF-II, EGF, bFGF, or KGF);

G) FN type-I Domains 1-5 [linker] FN type-III Domain 8 [linker] Growth Factor (IGF-I, IGF-II, EGF, bFGF, or KGF);

H) FN type-I Domains 1-5 [linker] FN type-III Domains 8-9 [linker] Growth Factor (IGF-I, IGF-II, EGF, bFGF, or KGF);

I) FN type-I Domains 1-5 [linker] EN type-III Domains 8-10 [linker] Growth Factor (IGF-I, IGF-II, EGF, bFGF, or KGF);

J) FN type-I Domains 1-5 [linker] FN type-III Domain 9 [linker] Growth Factor (IGF-I, IGF-II, EGF, bFGF, or KGF);

K) EN type-I Domains 1-5 [linker] FN type-III Domains 9-10 [linker] Growth Factor (IGF-I, IGF-II, EGF, bFGF, or KGF);

L) FN type-I Domains 1-5 [linker] FN type-III Domain 10 [linker] Growth Factor (IGF-I, IGF-II, EGF, bFGF, or KGF);

M) FN type-I Domains 4-5 [linker] FN type-III Domain 8 [linker] Growth Factor (IGF-I, IGF-II, EGF, bFGF, or KGF);

N) FN type-I Domains 4-5 [linker] FN type-III Domains 8-9 [linker] Growth Factor (IGF-I, IGF-II, EGF, bFGF, or KGF);

O) FN type-I Domains 4-5 [linker] FN type-III Domains 8-10 [linker] Growth Factor (IGF-I, IGF-II, EGF, bFGF, or KGF);

P) FN type-I Domains 4-5 [linker] FN type-III Domain 9 [linker] Growth Factor (IGF-I, IGF-II, EGF, bFGF, or KGF);

Q) FN type-I Domains 4-5 [linker] FN type-III Domains 9-10 [linker] Growth Factor (IGF-I, IGF-II, EGF, bFGF, or KGF);

R) FN type-I Domains 4-5 [linker] FN type-III Domain 10 [linker] Growth Factor (IGF-I, IGF-II, EGF, bFGF, or KGF).

Human FN, IGF-I, IGF-II, EGF, bFGF, and KGF gene DNA sequences (SEQ ID NOs: 1-6, respectively) can be codon-optimised for expression in *Spodoptera frugiperda*. The coding sequences can then be cloned into an expression vector incorporating a poly-histidine affinity tag to aid in the purification of the chimeras (e.g., the pIB/V5-His expression vector (Invitrogen)). A nucleotide sequence encoding an amino acid linker as discussed above can be inserted via site-directed mutagenesis PCR. The addition of an Asn to the C-terminus of the linker sequence can be used to generate a Asn-Gly motif with Gly being the first amino acid of the growth factor protein. This motif enables hydroxylamine induced cleavage of the growth factor protein from the chimeras.

The resulting constructs will encode various lengths of the FN protein linked by a linker to the full-length mature IGF-I, IGF-II, EGF, bFGF, or KGF proteins, or at least a domain of the IGF-I, IGF-II, EGF, bFGF, or KGF proteins capable of binding a cognate growth factor receptor. The DNA sequence of all constructs can be verified to ensure that the fidelity of the desired DNA sequences are maintained.

Clones in the pIB/V5-His vector can be used to transfect Sf9 insect cells and transiently-expressed secreted protein is detected in the conditioned media, as assessed by immunoblotting. Briefly, the samples are resolved on SDS-PAGE under reducing conditions and the proteins are transferred onto a nitrocellulose membrane using a semi-dry transfer method. The membrane is interrogated with poly-clonal anti-FN antibodies and the target protein species are then visualized using enhanced chemiluminescence.

Purification of the chimeric proteins is based on Ni-NTA Superflow Agarose (QIAGEN, Australia) affinity chromatography performed according to the manufacturer's instructions. The chimeric proteins are monitored throughout the purification process by SDS-PAGE and western blot analysis using a poly-clonal anti-FN antibody (Calbiochem).

Cells, such as MCF-10A cells, MCF-7 cells, and isolated human epithelial cells, keratinocytes and fibroblasts can be used to examine the effects of the synthetic chimeric proteins on cell migration and/or proliferation. For example, cell migration can be assessed using Transwell™ migration assays, while cell proliferation can be determined using cell proliferation assays well known to one of skill in the art.

Throughout the specification the aim has been to describe the preferred embodiments of the invention without limiting the invention to any one embodiment or specific collection of features. It will therefore be appreciated by those of skill in the art that, in light of the instant disclosure, various modifications and changes can be made in the particular embodiments exemplified without departing from the scope of the present invention.

All computer programs, algorithms, patent and scientific literature referred to herein are incorporated herein by reference.

TABLE I

| Fibronectin domains and regions | | |
|---|---|---|
| Position | Length | Description |
| 50-90 | 41 | Fibronectin type-I 1 |
| 95-138 | 44 | Fibronectin type-I 2 |
| 139-182 | 44 | Fibronectin type-I 3 |
| 184-228 | 45 | Fibronectin type-I 4 |
| 229-273 | 45 | Fibronectin type-I 5 |
| 306-345 | 40 | Fibronectin type-I 6 |
| 355-403 | 49 | Fibronectin type-II 1 |
| 415-463 | 49 | Fibronectin type-II 2 |
| 468-511 | 44 | Fibronectin type-I 7 |
| 516-558 | 43 | Fibronectin type-I 8 |
| 559-602 | 44 | Fibronectin type-I 9 |
| 607-699 | 93 | Fibronectin type-III 1 |
| 720-809 | 90 | Fibronectin type-III 2 |
| 811-898 | 88 | Fibronectin type-III 3 |
| 908-995 | 88 | Fibronectin type-III 4 |
| 996-1084 | 89 | Fibronectin type-III 5 |
| 1087-1172 | 86 | Fibronectin type-III 6 |
| 1173-1265 | 93 | Fibronectin type-III 7 |
| 1266-1356 | 91 | Fibronectin type-III 8 |
| 1357-1446 | 90 | Fibronectin type-III 9 |
| 1447-1536 | 90 | Fibronectin type-III 10 |
| 1541-1630 | 90 | Fibronectin type-III 11 |
| 1631-1720 | 90 | Fibronectin type-III 12 |
| 1723-1810 | 88 | Fibronectin type-III 13 |
| 1813-1901 | 89 | Fibronectin type-III 14 |
| 1902-1991 | 90 | Fibronectin type-III 15 |
| 2100-2190 | 91 | Fibronectin type-III 16 |
| 2204-2248 | 45 | Fibronectin type-I 10 |
| 2249-2291 | 43 | Fibronectin type-I 11 |
| 2293-2336 | 44 | Fibronectin type-I 12 |
| 907-1172 | 266 | DNA-binding |
| 52-272 | 221 | Fibrin- and heparin-binding 1 |
| 308-608 | 301 | Collagen-binding |
| 464-477 | 14 | Critical for collagen binding |
| 1267-1540 | 274 | Cell-attachment |
| 1721-1991 | 271 | Heparin-binding 2 |
| 1813-1991 | 179 | Binds to FBLN1 |
| 1992-2102 | 111 | Connecting strand 3 (CS-3) (V region) |
| 2206-2337 | 132 | Fibrin-binding 2 |

The invention claimed is:

1. An isolated protein complex in the form of a synthetic chimeric protein consisting of an amino acid sequence of:
   (i) a growth factor or at least a domain of said growth factor which is capable of binding a cognate growth factor receptor;
   (ii) an optional linker sequence; and
   (iii) domain 10 of fibronectin (FN), wherein domain 10 consists of amino acids 1447-1536 of the amino acid sequence set forth in SEQ ID NO: 1.

2. The isolated protein complex of claim 1, wherein said growth factor is selected from insulin-like growth factor-1 (IGF-I), insulin-like growth factor-II (IGF-II), epidermal growth factor (ESE), and basic fibroblast growth factor (bFGF).

3. The isolated protein complex of claim 1, wherein the linker sequence comprises a protease cleavage site.

4. The isolated protein complex of claim 1, wherein the linker sequence is selected from the group consisting of:

| (i)   | Gly$_4$Ser       | (SEQ ID NO: 7) |
| (ii)  | Gly$_4$Ser$_3$   | (SEQ ID NO: 8) |
| (iii) | (Gly$_4$Ser)$_3$ | (SEQ ID NO: 9) |
| (iv)  | (Gly$_4$Ser)$_4$ | (SEQ ID NO: 7) |
| (iv) and | Leu Ile Lys Met Lys Pro; | (SEQ ID NO: 11) |
| (vi)  | Gln Pro Gln Gly Leu Ala Lys. | (SEQ ID NO: 12) |

5. An isolated nucleic acid encoding the isolated protein complex of claim 1.

6. A genetic construct, comprising the isolated nucleic acid of claim 5 operably linked to one or more regulatory nucleotide sequences in a vector.

7. The genetic construct of claim 6, which is an expression construct, wherein the isolated nucleic acid is operably linked to a promoter.

8. An isolated host cell, comprising the genetic construct of claim 6.

9. A pharmaceutical composition, comprising the isolated protein complex of claim 1 and a pharmaceutically-acceptable carrier, diluent or excipient.

10. A surgical implant, scaffold or prosthesis impregnated, coated or otherwise comprising the isolated protein complex of claim 1.

11. A wound or burn dressing, comprising the isolated protein complex of claim 1.

* * * * *